(12) United States Patent
Yoo et al.

(10) Patent No.: US 12,089,495 B2
(45) Date of Patent: Sep. 10, 2024

(54) ORGANIC COMPOUND AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Seon Keun Yoo, Paju-si (KR); Ji Cheol Shin, Paju-si (KR); Jeong Dae Seo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 666 days.

(21) Appl. No.: 17/288,784

(22) PCT Filed: Aug. 31, 2020

(86) PCT No.: PCT/KR2020/011637
§ 371 (c)(1),
(2) Date: Apr. 26, 2021

(87) PCT Pub. No.: WO2021/049799
PCT Pub. Date: Mar. 18, 2021

(65) Prior Publication Data
US 2021/0408395 A1    Dec. 30, 2021

(30) Foreign Application Priority Data
Sep. 11, 2019  (KR) .................. 10-2019-0113136

(51) Int. Cl.
*H10K 85/50*    (2023.01)
*C07D 471/04*    (2006.01)
(Continued)

(52) U.S. Cl.
CPC ....... *H10K 85/6572* (2023.02); *C07D 471/04* (2013.01); *C09K 11/06* (2013.01);
(Continued)

(58) Field of Classification Search
CPC ............ H10K 85/626; H10K 85/6572; C07D 471/04; C09K 11/06
See application file for complete search history.

(56) References Cited

U.S. PATENT DOCUMENTS

| | | | |
|---|---|---|---|
| 2015/0303380 A1* | 10/2015 | Kambe | H10K 85/626 257/40 |
| 2016/0197289 A1* | 7/2016 | Sado | C07D 401/14 257/40 |
| 2018/0166647 A1 | 6/2018 | Shin et al. | |
| 2019/0181354 A1 | 6/2019 | Shin et al. | |

(Continued)

FOREIGN PATENT DOCUMENTS

| CN | 108218858 A |   | 6/2018 |
|---|---|---|---|
| CN | 108558874 A | * | 9/2018 |

(Continued)

OTHER PUBLICATIONS

International Search Report dated Dec. 1, 2020, issued in International Patent Application No. PCT/KR2020/011637.
(Continued)

*Primary Examiner* — Amanda C. Walke
(74) *Attorney, Agent, or Firm* — Morgan, Lewis & Bockius LLP

(57) ABSTRACT

The present disclosure relates to an organic compound including a substituted or non-substituted phenanthroline moiety and a substituted or non-substituted anthracene moiety and being partially deuterated and an organic light emitting diode includes the organic compound. The organic compound has improved electron transporting property and/or the charge generation property. According, the emitting efficiency and the lifespan of the OLED and the organic light emitting display device including the organic compound in the ETL and/or the CGL are improved.

17 Claims, 6 Drawing Sheets

(51) Int. Cl.
  *C09K 11/06* (2006.01)
  *H10K 85/60* (2023.01)
  *H10K 50/13* (2023.01)
  *H10K 50/16* (2023.01)
(52) U.S. Cl.
  CPC ........ *H10K 85/626* (2023.02); *C07B 2200/05* (2013.01); *C09K 2211/1018* (2013.01); *H10K 50/131* (2023.02); *H10K 50/16* (2023.02)

(56) References Cited

U.S. PATENT DOCUMENTS

2020/0013961 A1* 1/2020 Kim .................... H10K 85/655
2020/0373501 A1  11/2020 Zhang et al.

FOREIGN PATENT DOCUMENTS

| | | | |
|---|---|---|---|
| CN | 110041159 A | * | 7/2019 |
| CN | 110128424 A | | 8/2019 |
| JP | 2014123687 A | | 7/2014 |
| KR | 10-20140095728 A | | 8/2014 |
| KR | 10-20180067321 A | | 6/2018 |
| KR | 10-20190053354 A | | 5/2019 |
| KR | 10-2019-0070795 A | | 6/2019 |

OTHER PUBLICATIONS

Office Action Report dated Jan. 11, 2023, issued in China Patent Application No. 202080004811.2.

* cited by examiner

【Figure 1】
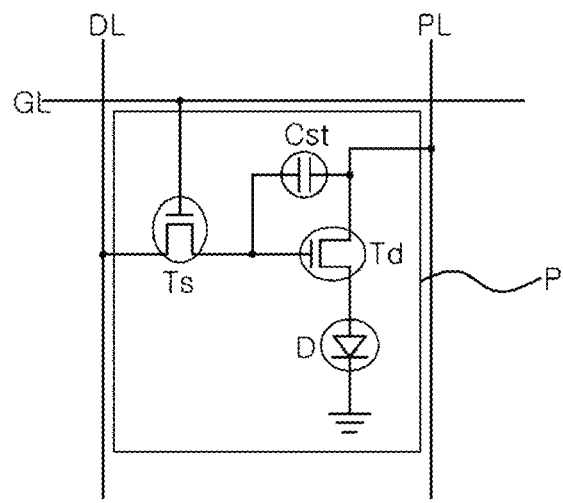

【Figure 2】
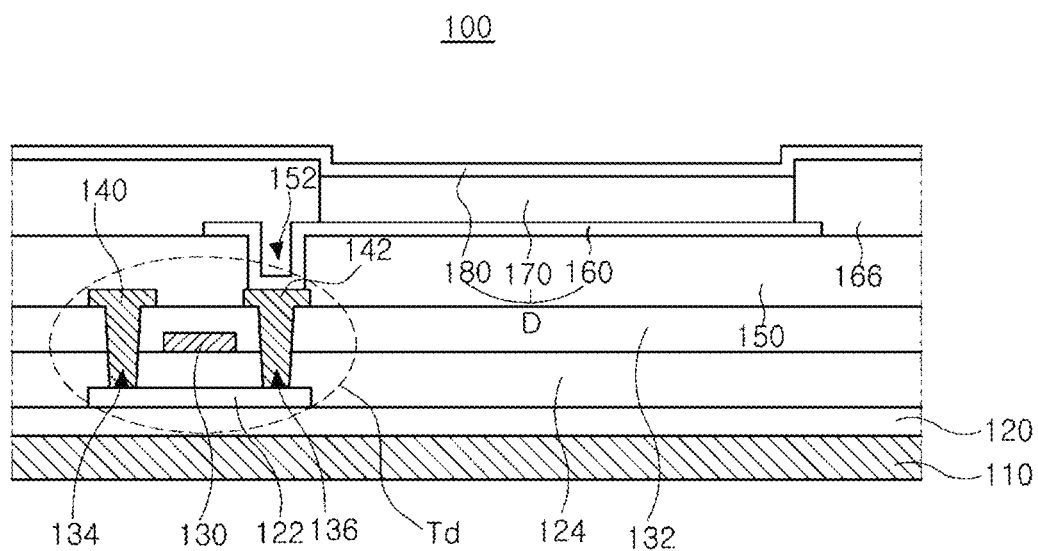

[Figure 3]
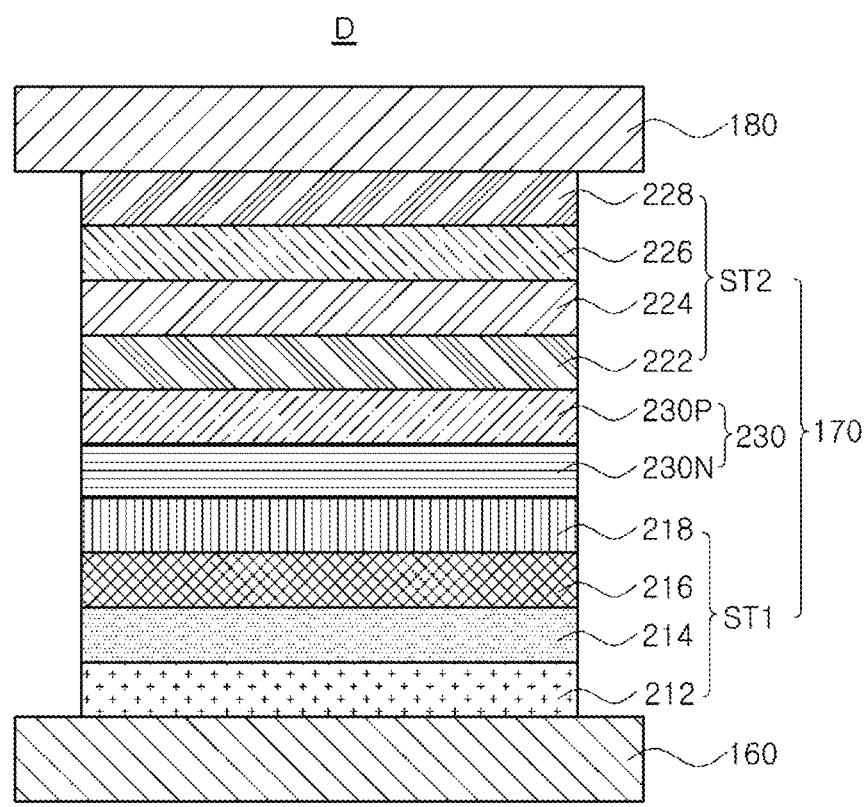

[Figure 4]
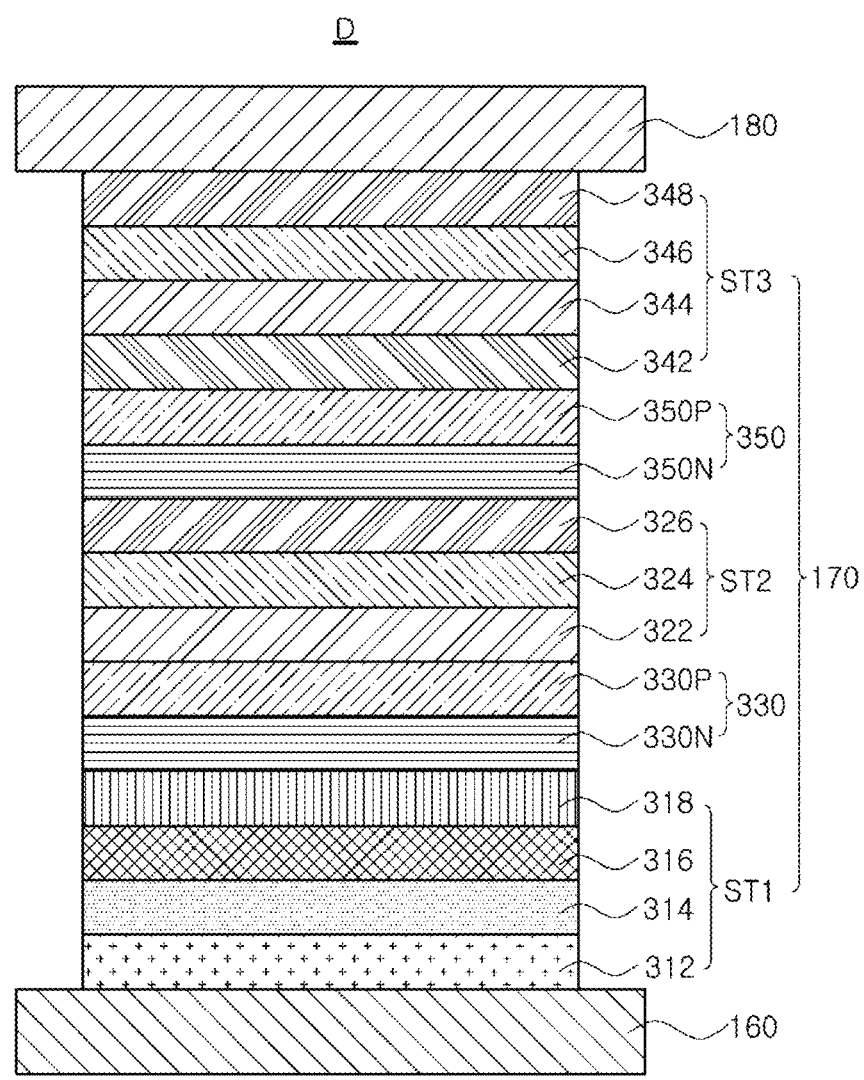

[Figure 5]
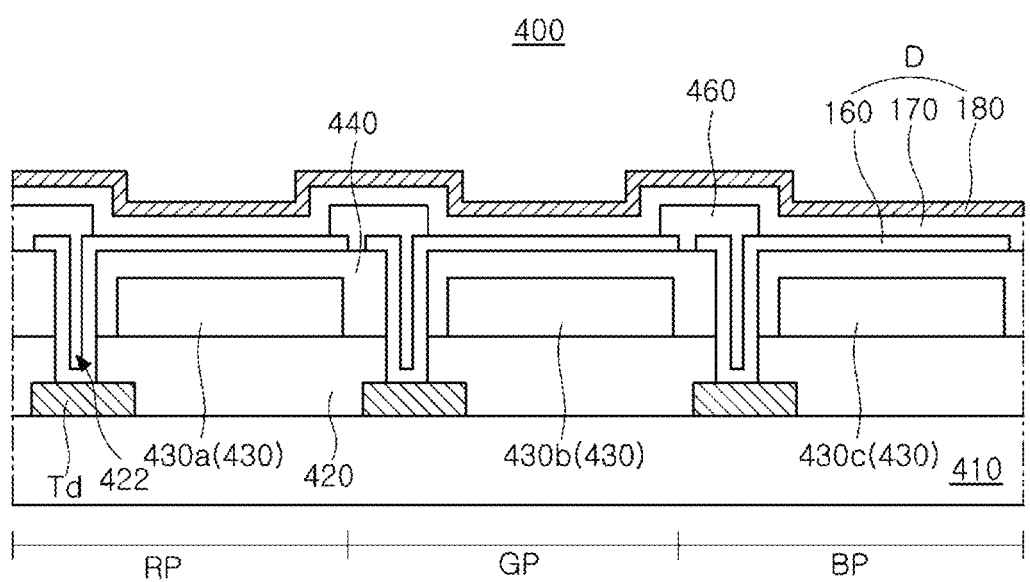

[Figure 6]
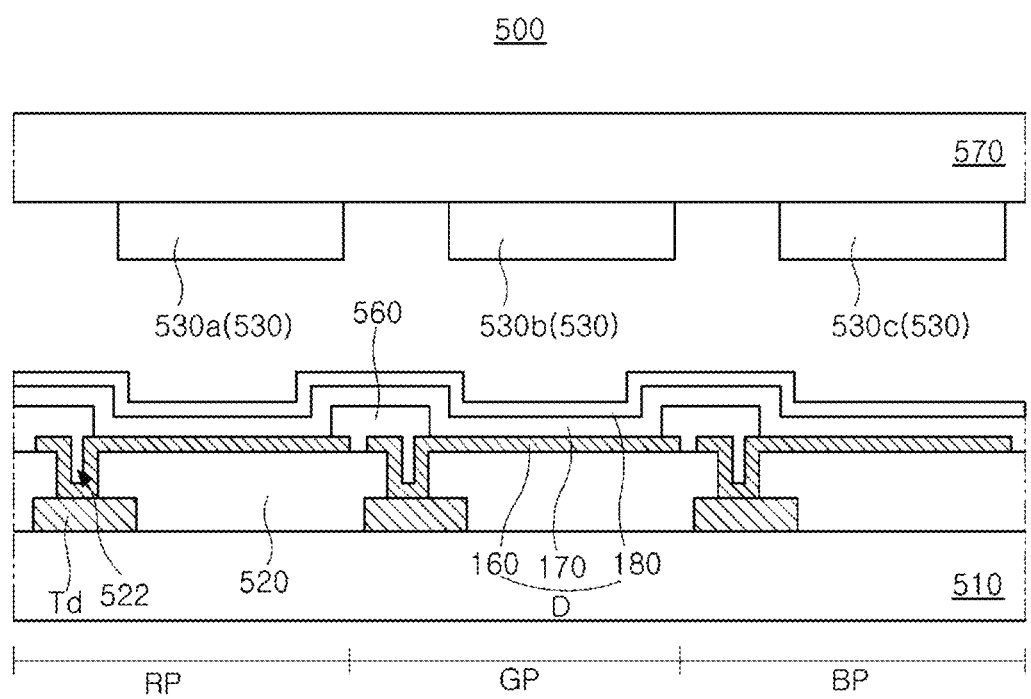

ORGANIC COMPOUND AND ORGANIC LIGHT EMITTING DIODE AND ORGANIC LIGHT EMITTING DISPLAY DEVICE INCLUDING THE SAME

TECHNICAL FIELD

The present disclosure relates to an organic compound, and more specifically, to an organic compound being used for an electron auxiliary layer and/or an n-type charge generation layer and being capable of increasing an emitting efficiency and a lifespan of an organic light emitting diode and an organic light emitting display device including the same.

BACKGROUND ART

As requests for flat panel display devices having a small occupied area have been increased, an organic light emitting display device, which may be referred to as an organic electroluminescent device (OELD), including an organic light emitting diode (OLED) among the flat panel display device has been the subject of recent research and development.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. In addition, the organic light emitting display device can be operated at a voltage (e.g., 10V or below) lower than a voltage required to operate other display devices. Moreover, the organic light emitting display device has advantages in the power consumption and the color purity.

An organic emitting layer of the OLED may include an electron transporting layer (ETL) with the EML. In addition, to provide a white OLED (W-OLED), the OLED may have a multi-stack structure including a charge generation layer (CGL).

However, sufficient development has not been made for materials used for the ETL and/or the CGL, and there is a limitation in the emitting efficiency and the lifespan of the OLED.

DISCLOSURE

Technical Problem

Accordingly, the present disclosure is directed to an organic compound, an OLED and an organic light emitting display device that substantially obviate one or more of the problems due to the limitations and disadvantages of the related art.

An object of the present disclosure is to provide an organic compound being used for an electron auxiliary layer and/or an n-type charge generation layer and being capable of increasing an emitting efficiency and a lifespan of an organic light emitting diode and an organic light emitting display device including the same.

Another object of the present disclosure is to provide an OLED and an organic light emitting display device having enhanced emitting efficiency and lifespan.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

Technical Solution

According to an aspect, the present disclosure provides an organic compound of Formula, wherein A is phenanthroline, and B is anthracene, wherein $L_1$ is selected from a C6 to C30 arylene group, and $L_2$ is selected from a C6 to C30 aryl group, a C6 to C30 arylene group, a C5 to C30 heteroaryl group and a C5 to C30 heteroarylene group, and each of $R_1$ and $R_2$ is independently selected from a C1 to C10 alkyl group, a C6 to C30 aryl group and a C5 to C30 heteroaryl group, wherein each of a, b, c and d is independently 0 (zero) or a positive integer, and wherein a part of hydrogens in A, B, L1, L2, R1 and R2 is substituted by deuterium.

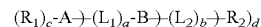

According to another aspect, the present disclosure provides an organic light emitting diode that includes a first electrode; a second electrode facing the first electrode; an emitting material layer positioned between the first and second electrodes; a hole auxiliary layer positioned between the first electrode and the emitting material layer; and an electron auxiliary layer positioned between the emitting material layer and the second electrode, wherein the electron auxiliary layer includes the organic compound.

According to another aspect, the present disclosure provides an organic light emitting diode that includes a first electrode; a second electrode facing the first electrode; a first emitting part positioned between the first and second electrodes and including a first emitting material layer; a second emitting part positioned between the first emitting material layer and the second electrode and including a second emitting material layer; and a first charge generation layer between the first and second emitting parts, wherein the first charge generation layer includes the organic compound.

It is to be understood that both the foregoing general description and the following detailed description are examples and are explanatory and are intended to provide further explanation of the disclosure as claimed.

Advantageous Effects

An organic compound of the present disclosure includes a substituted or non-substituted phenanthroline moiety and a substituted or non-substituted anthracene moiety combined (connected or bonded) to the phenanthroline moiety through a linker or directly, and a part of hydrogens of the phenanthroline moiety, the substituent of the phenanthroline moiety, the anthracene moiety, the substituent of the anthracene moiety and the linker is deuterated. The electron transporting property and/or the charge generation property of the organic compound are improved.

According, the emitting efficiency and the lifespan of the OLED and the organic light emitting display device including the organic compound in the ETL and/or the CGL are improved.

DESCRIPTION OF DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

FIG. 1 is a schematic circuit diagram illustrating an organic light emitting display device of the present disclosure.

FIG. 2 is a schematic cross-sectional view illustrating an organic light emitting display device according to the present disclosure.

FIG. 3 is a schematic cross-sectional view illustrating an OLED of the present disclosure.

FIG. 4 is a schematic cross-sectional view illustrating an OLED of the present disclosure.

FIG. 5 is a schematic cross-sectional view illustrating an organic light emitting display device according to the present disclosure.

FIG. 6 is a schematic cross-sectional view illustrating an organic light emitting display device according to the present disclosure.

MODE FOR INVENTION

Reference will now be made in detail to aspects of the disclosure, examples of which are illustrated in the accompanying drawings.

FIG. 1 is a schematic circuit diagram illustrating an organic light emitting display device of the present disclosure.

As illustrated in FIG. 1, a gate line GL and a data line DL, which cross each other to define a pixel region P, and a power line PL are formed in an organic light display device. A switching thin film transistor (TFT) Ts, a driving TFT Td, a storage capacitor Cst and an OLED D are formed in the pixel region P.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Tr. The OLED D emits light having a luminance proportional to the current flowing through the driving thin film transistor Td. In this case, the storage capacitor Cst is charge with a voltage proportional to the data signal so that the voltage of the gate electrode in the driving thin film transistor Td is kept constant during one frame.

Therefore, the organic light emitting display device can display a desired image.

FIG. 2 is a schematic cross-sectional view illustrating an organic light emitting display device according to the present disclosure.

As illustrated in FIG. 2, the organic light emitting display device 100 includes a substrate 110, a driving TFT Td and an OLED D connected to the driving TFT Td.

The substrate 110 may be a glass substrate or a plastic substrate. For example, the substrate 110 may be a polyimide substrate.

A buffer layer 120 is formed on the substrate, and the driving TFT Td is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the driving TFT Td.

In the driving TFT Td, the gate electrode 130, the source electrode 140, and the drain electrode 142 are positioned over the semiconductor layer 122. Namely, the TFT Tr has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

Although not shown, the gate line and the data line cross each other to define the pixel region, and the switching TFT Ts (of FIG. 1) is formed to be connected to the gate and data lines. The switching TFT Ts is connected to the driving TFT Td.

In addition, the power line, which may be formed to be parallel to and spaced apart from one of the gate and data lines, and the storage capacitor for maintaining the voltage of the gate electrode of the TFT Tr in one frame may be further formed.

A passivation layer 150, which includes a drain contact hole 152 exposing the drain electrode 142 of the driving TFT Td, is formed to cover the driving TFT Td.

A first electrode 160, which is connected to the drain electrode 142 of the driving TFT Td through the drain contact hole 152, is separately formed in each pixel. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the organic light emitting display device 100 is operated in a top-emission type, a reflection electrode or a reflection layer may be formed under the first electrode 160. For example, the reflection electrode or the reflection layer may be formed of aluminum-palladium-copper (APC) alloy.

A bank layer 166 is formed on the passivation layer 150 to cover an edge of the first electrode 160. Namely, the bank layer 166 is positioned at a boundary of the pixel and exposes a center of the first electrode 160 in the pixel.

An organic emitting layer 170 is formed on the first electrode 160. The organic emitting layer 170 is positioned in each pixel region P. For example, the organic emitting layer 170 may include a red emitting layer in a red pixel region, a green emitting layer in a green pixel region and a blue emitting layer in a blue pixel region.

A second electrode 180 is formed over the substrate 110 where the organic emitting layer 170 is formed. The second electrode 180 covers an entire surface of the display area and may be formed of a conductive material having a relatively low work function to serve as a cathode. For example, the second electrode 180 may be formed of aluminum (Al), magnesium (Mg) or Al—Mg alloy.

The first electrode 160, the organic emitting layer 170 and the second electrode 180 constitute the OLED D.

The organic emitting layer 170 includes an organic compound of the present disclosure. For example, the organic emitting layer 170 may include an emitting material layer (EML) between the first and second electrodes 160 and 180, a hole auxiliary layer between the first electrode 160 and the EML and an electron auxiliary layer between the second electrode 180 and the EML, and the organic compound of the present disclosure may be included in the electron auxiliary layer.

The organic compound of the preset disclosure is represented by Formula 1.

   Formula 1

In Formula 1, A is phenanthroline, and B is anthracene. $L_1$ is selected from a C6 to C30 arylene group, and $L_2$ is selected from a C6 to C30 aryl group, a C6 to C30 arylene group, a C5 to C30 heteroaryl group and a C5 to C30 heteroarylene group. Each of $R_1$ and $R_2$ is independently selected from a C1 to C10 alkyl group, a C6 to C30 aryl group and a C5 to C30 heteroaryl group. In addition, each of a, b, c and d is independently 0 (zero) or a positive integer.

In this instance, a part of the hydrogens in A, B, $L_1$, $L_2$, $R_1$ and $R_2$ is deuterated. Namely, a part of the hydrogens in A, B, $L_1$, $L_2$, $R_1$ and $R_2$ is substituted by deuterium, and the rest of the hydrogens in A, B, $L_1$, $L_2$, $R_1$ and $R_2$ is non-substituted.

The organic compound of the present disclosure includes a substituted or non-substituted phenanthroline moiety and a substituted or non-substituted anthracene moiety combined (connected or bonded) to the phenanthroline moiety through a linker or directly, and a part of hydrogens of the phenanthroline moiety, the substituent of the phenanthroline moiety, the anthracene moiety, the substituent of the anthracene moiety and the linker is deuterated.

For example, A in Formula 1 may be represented by Formula 2. One of $R_{11}$ to $R_{18}$ is substituted by L1, and each of the rest of $R_{11}$ to $R_{18}$ is selected from the group consisting of hydrogen, deuterium, CN, F, $CF_3$, $OCF_3$, C1 to C10 alkyl, deuterated C1 to C10 alkyl, C6 to C30 aryl, deuterated C6 to C30 aryl, C5 to C30 heteroaryl and deuterated C5 to C30 heteroaryl.

Formula 2

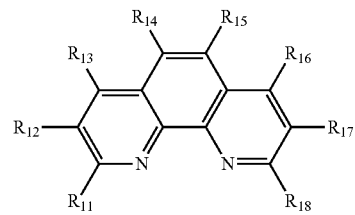

For example, each of the rest of $R_{11}$ to $R_{18}$ may be independently selected from the group consisting of hydrogen, deuterium, methyl, $CD_3$, phenyl, deuterated phenyl, naphthyl, deuterated naphthyl, pyridyl, deuterated pyridyl, quinolinyl, deuterated quinolinyl, iso-quinolinyl and deuterated iso-quinolinyl.

In Formula 1, c may be 0 or 1, and R1 may be selected methyl, phenyl, naphthyl, pyridyl, iso-quinolinyl, deuterated methyl ($CD_3$), phenyl substituted by $CD_3$, deuterated phenyl, deuterated naphthyl, deuterated pyridyl, deuterated quinolinyl, and deuterated iso-quinolinyl.

For example, a part of "$R_1$-A" in Formula 1 may be selected from Formula 3.

Formula 3

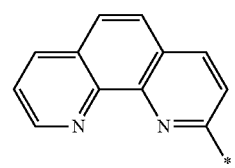

A-1

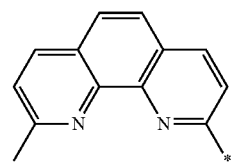

A-2

A-3 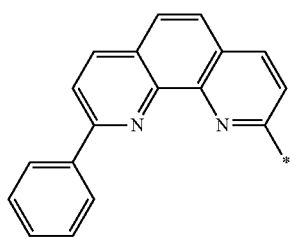
A-4 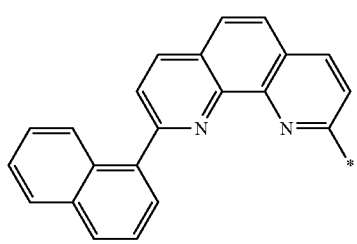
A-5 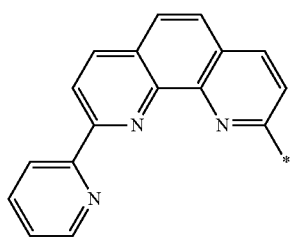
A-6 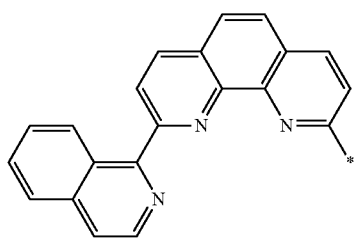
A-7 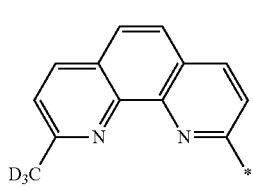
A-8 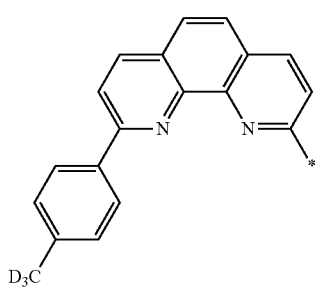
A-9 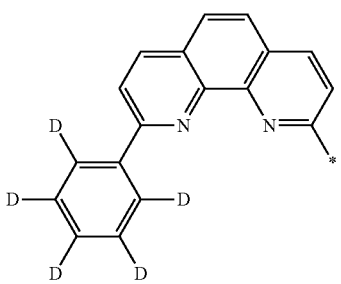
A-10 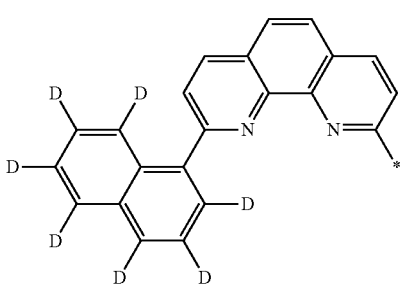
A-11 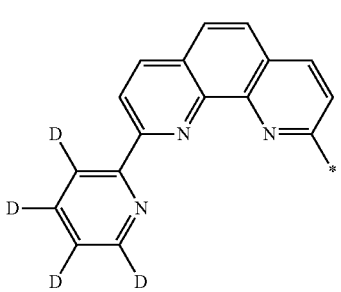
A-12 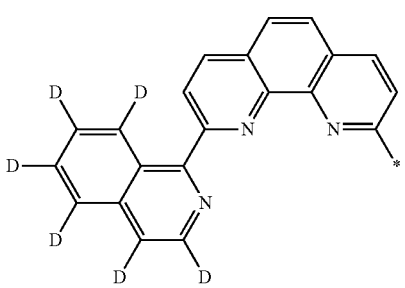
A-13 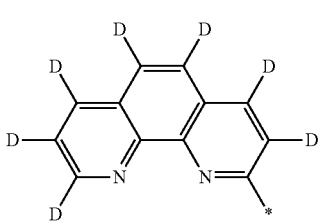

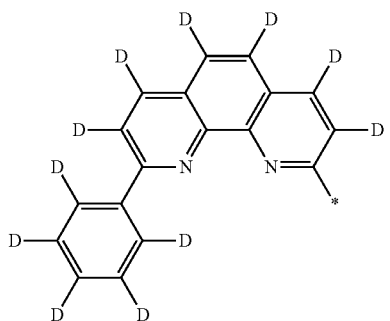

A-14

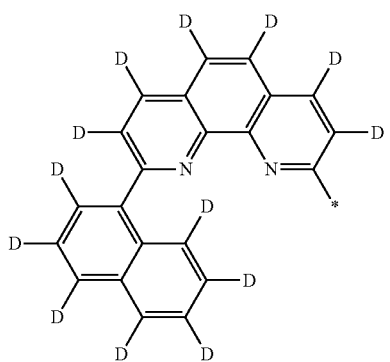

A-15

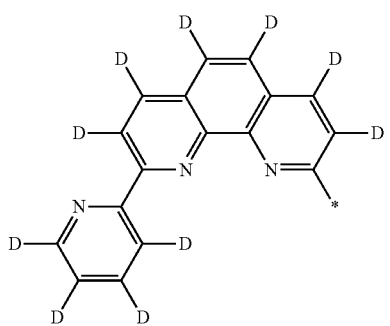

A-16

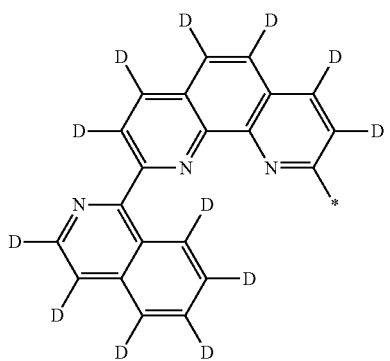

A-17

B in Formula 1 may be represented by Formula 4. One of R21 to R30 is substituted by L1, another one of R21 to R30 is substituted by $L_2$, and each of the rest of R21 to R30 is selected from the group consisting of hydrogen, deuterium, CN, F, $CF_3$, $OCF_3$, C1 to C10 alkyl, deuterated C1 to C10 alkyl, C6 to C30 aryl, deuterated C6 to C30 aryl, C5 to C30 heteroaryl and deuterated C5 to C30 heteroaryl.

Formula 4

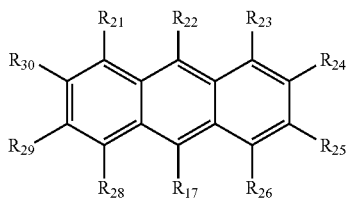

For example, each of the rest of $R_{21}$ to $R_{30}$ may be independently selected from the group consisting of hydrogen, deuterium, methyl, $CD_3$, phenyl, deuterated phenyl, naphthyl, deuterated naphthyl, pyridyl, deuterated pyridyl, quinolinyl, deuterated quinolinyl, iso-quinolinyl and deuterated iso-quinolinyl.

For example, B in Formula 1 may be selected from Formula 5.

Formula 5

B-1

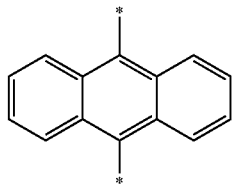

B-2

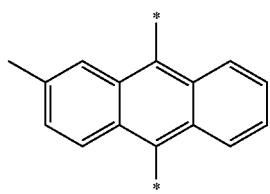

B-3

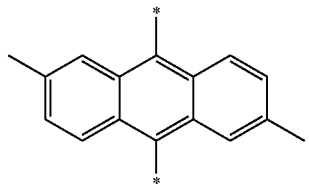

B-4

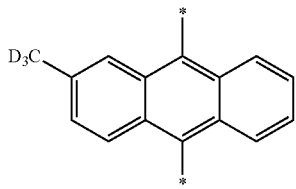

B-5

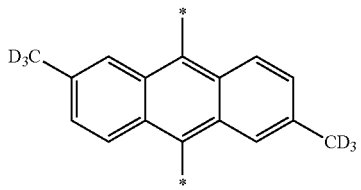

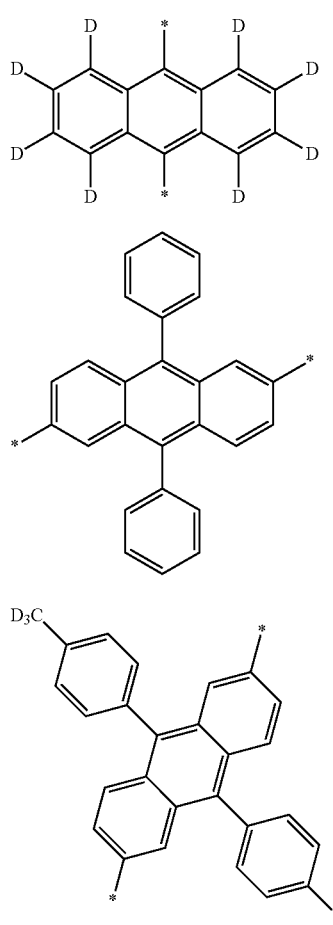

B-6

B-7

B-8

In Formula 1, a may be 1, and $L_1$ may be selected from phenylene, naphthylene, deuterated phenylene and deuterated naphthylene.

In addition, in Formula 1, b may be 1, and $L_2$ may be selected from phenyl, phenylene, naphthyl, naphthylene, pyridyl, pyridylene, deuterated phenyl, deuterated phenylene, deuterated naphthyl, deuterated naphthylene, deuterated pyridyl and deuterated pyridylene.

In Formula 1, d may be 0 or 1, and R2 may be selected from pyridyl, deuterated pyridyl, pyrimidyl and deuterated pyrimidyl.

For example, the organic compound in Formula 1 may be represented by Formula 6.

Formula 6

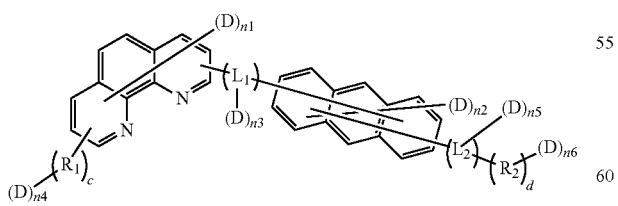

In Formula 6, each of c and d is independently 0 or 1, and each of n1 to n6 is independently 0 or a positive integer. In addition, at least one of n1 and n4 may be a positive integer, and n2, n5, and n6 may be 0. $L_1$, $L_2$, $R_1$, and $R_2$ are as defined in Chemical Formula 1.

For example, the organic compound of the present disclosure may be one of materials in Formula 7.

Formula 7

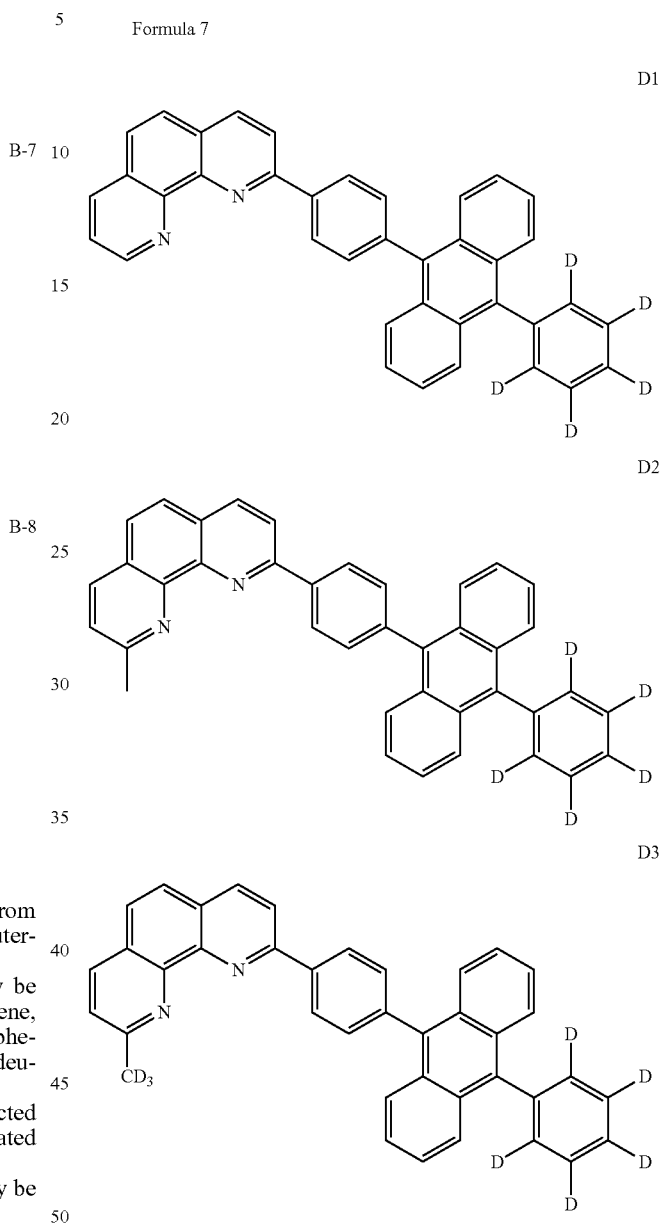

D1

D2

D3

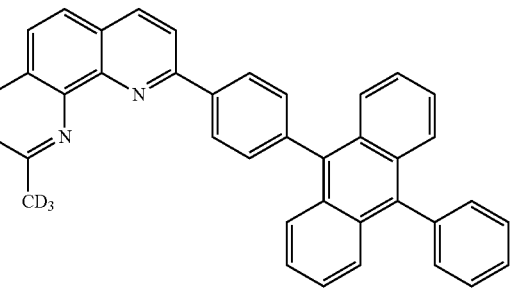

D4

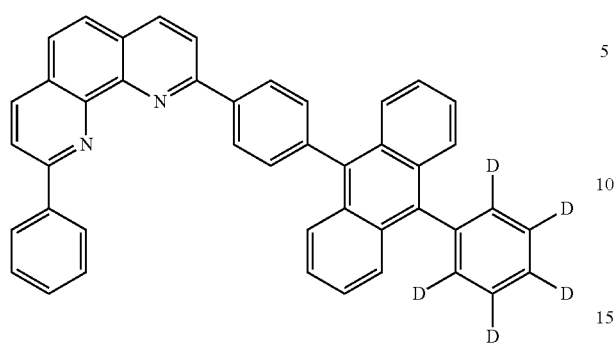
D5
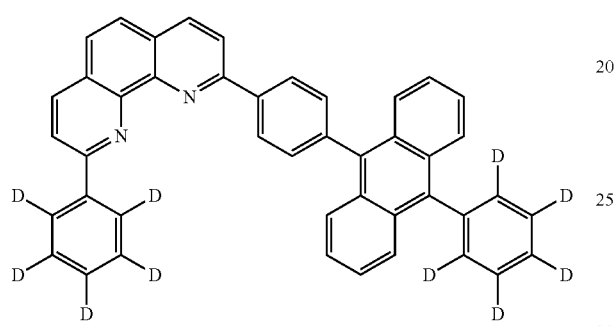
D6
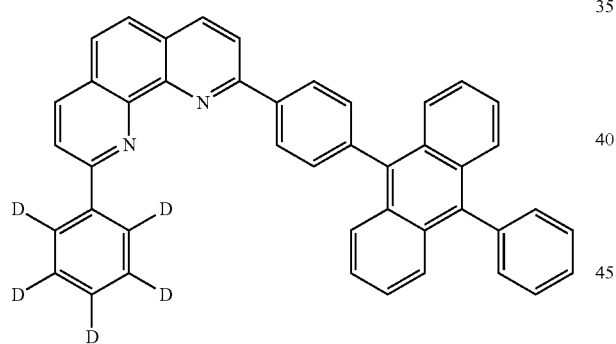
D7
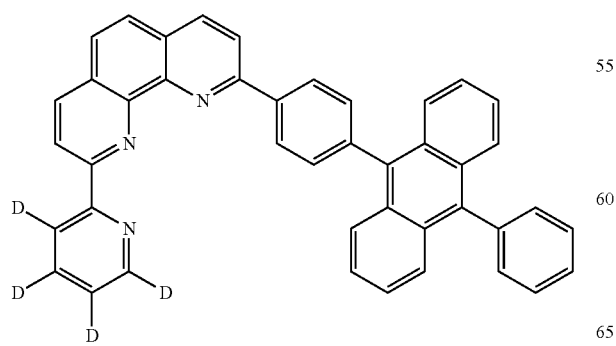
D8
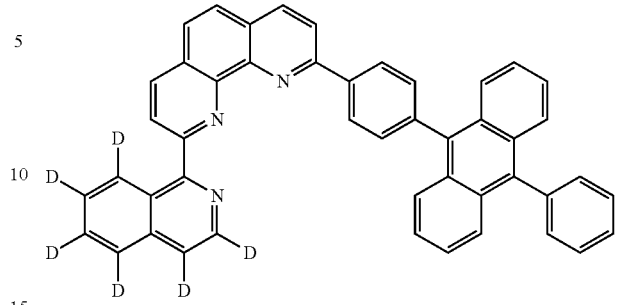
D9
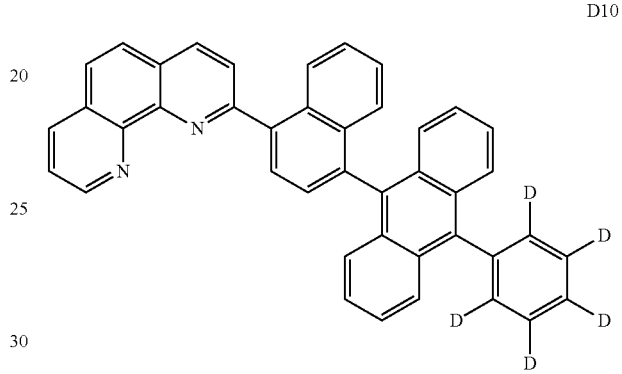
D10
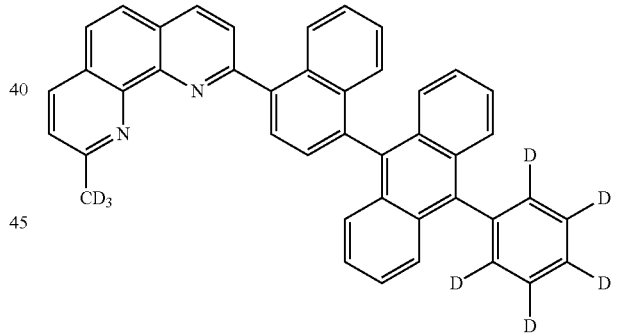
D11
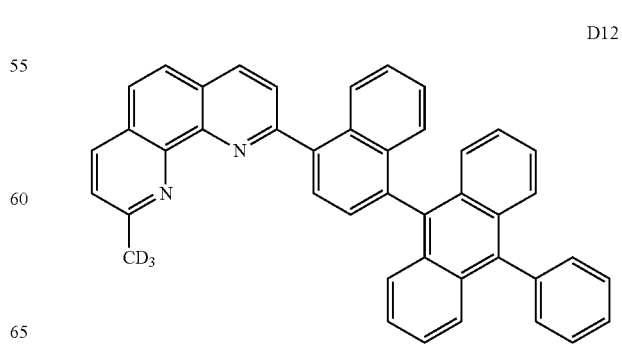
D12

D13
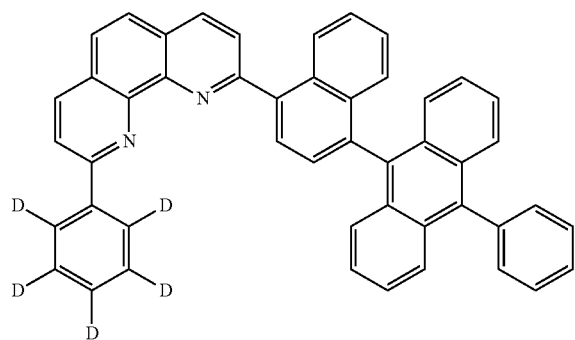
D14
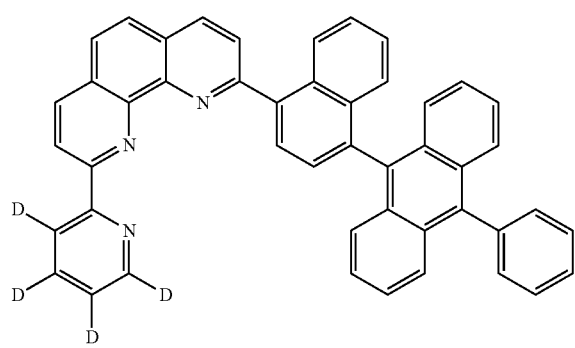
D15
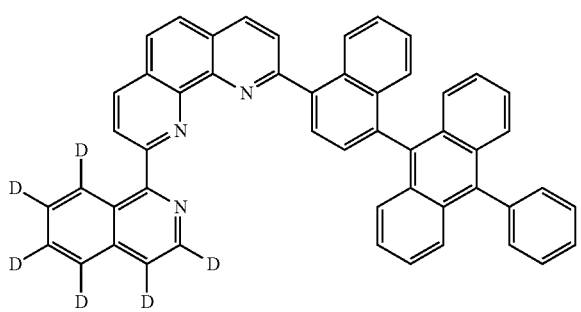
D16
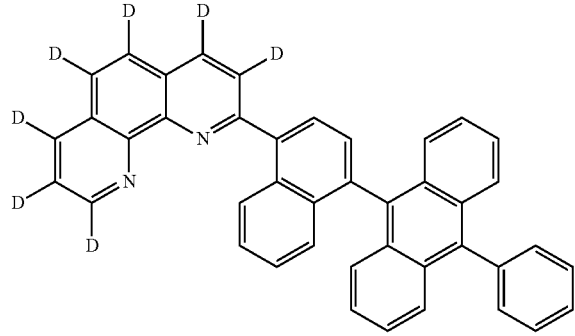
D17
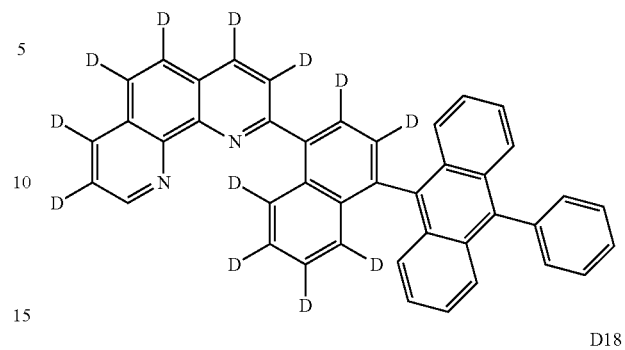
D18
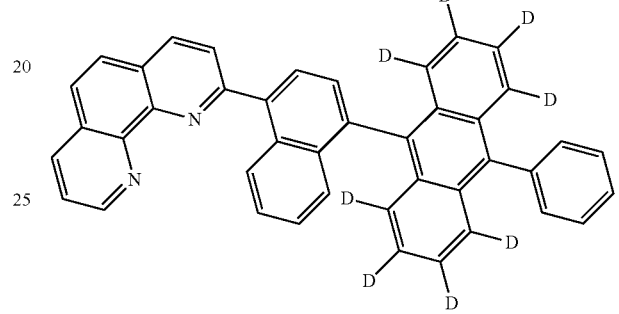
D19
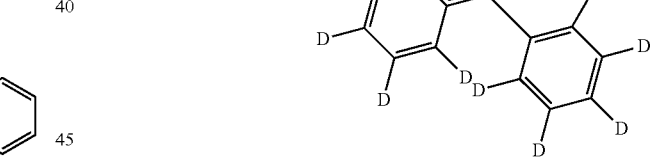
D20
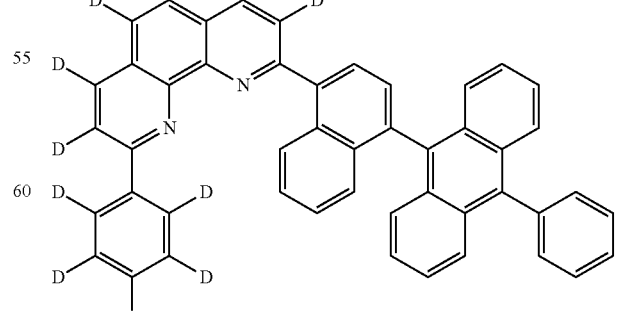

-continued
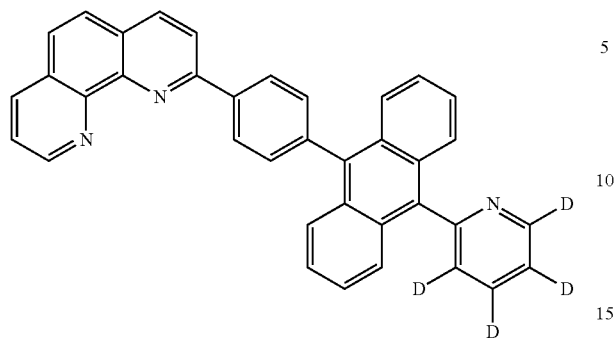
D21
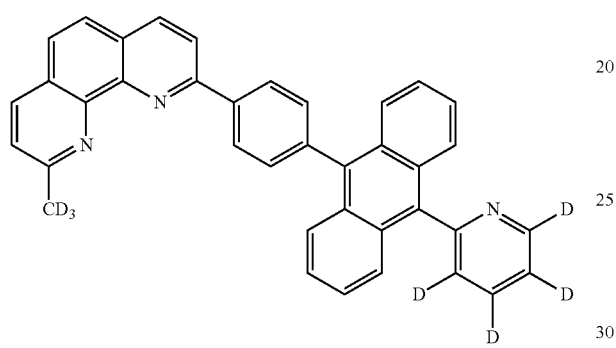
D22
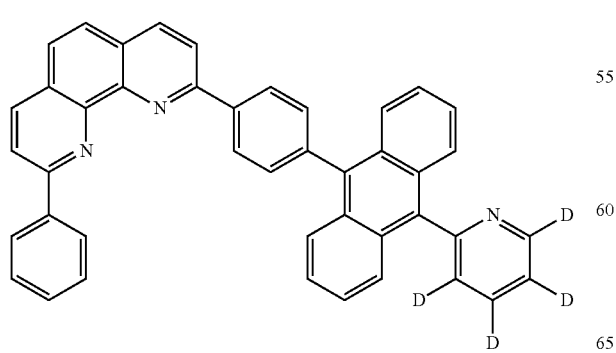
D23
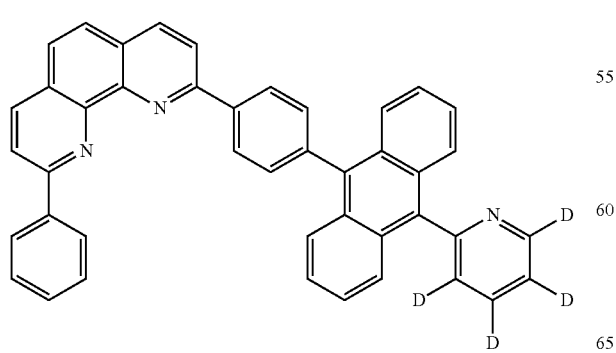
D24
-continued
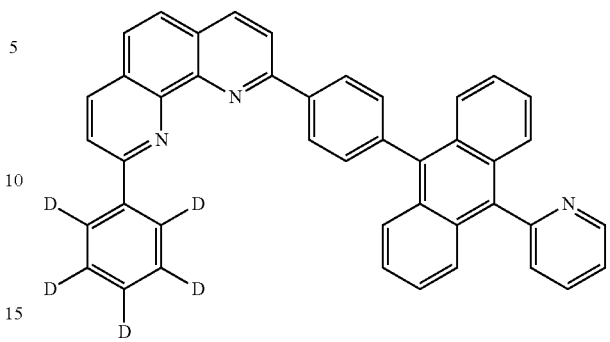
D25
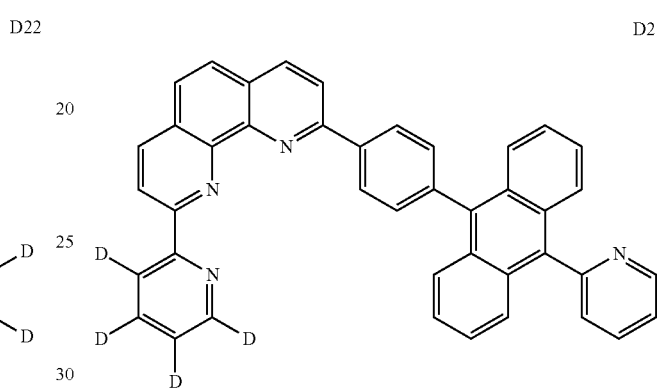
D26
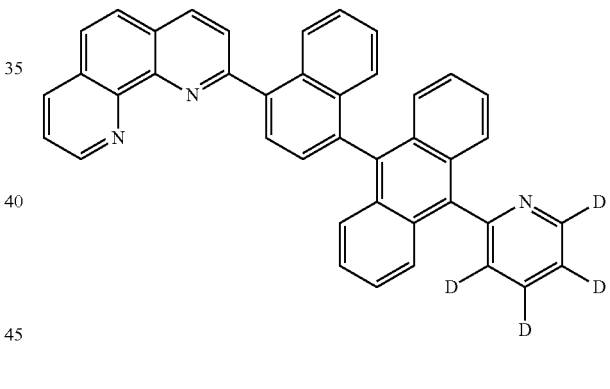
D27
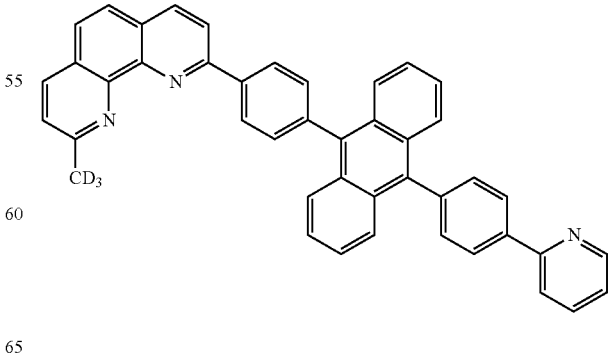
D28

-continued
D29
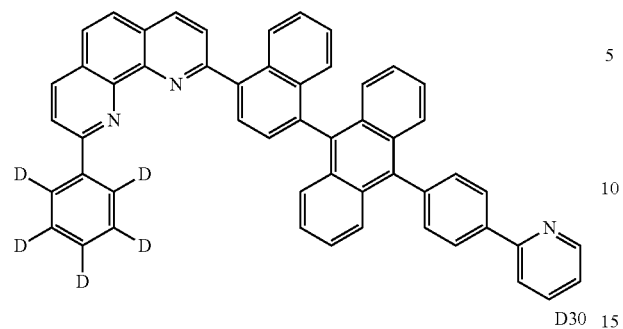
D30
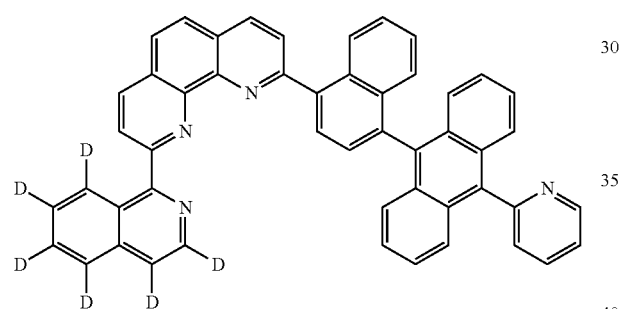
D31
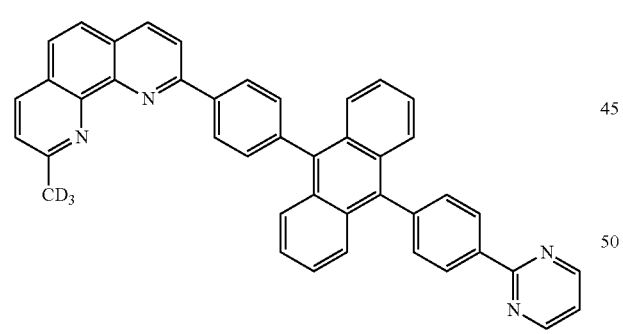
D32
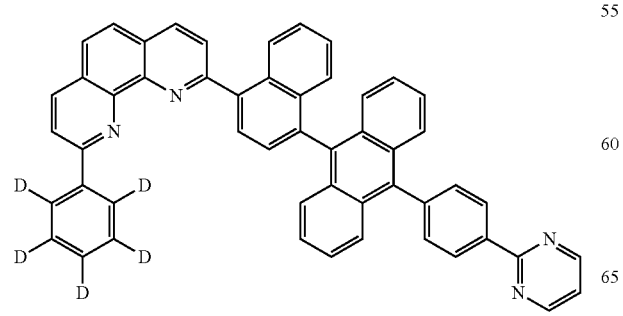
D33
-continued
D34
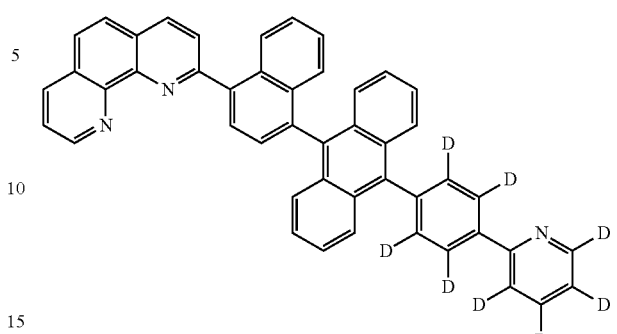
D35
D36
D37

21
-continued

D38

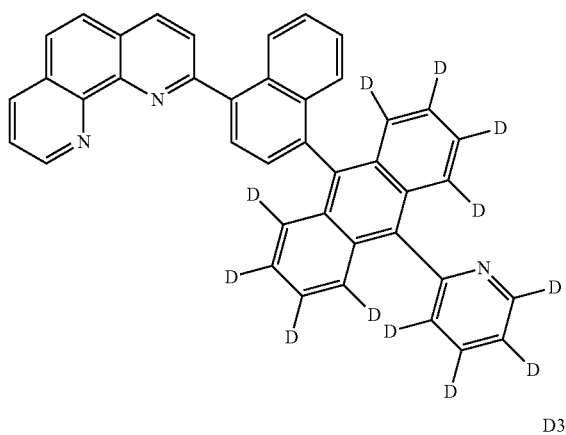

D39

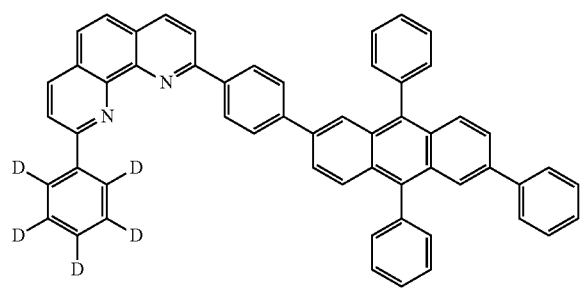

Synthesis of Organic Compound
1. Synthesis of Compound D10
(1) Intermediate 1

[Reaction Formula 1-1]

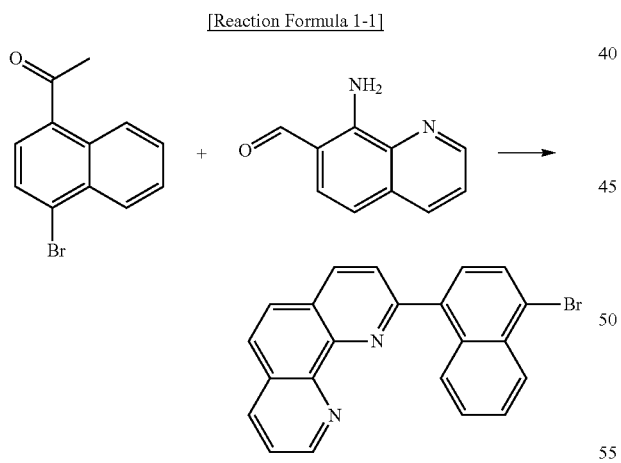

1-(1-bromonaphthalen-4-yl)ethanone (14.5 g, 0.058 mol), 8-aminoquinoline-7-carbaldehyde (10 g, 0.058 mol), ethanol(EtOH, 800 ml) and KOH (13 g) were put into the round-bottom flask and heated. The mixture was refluxed and stirred for 15 hrs. The reaction solution was cooled to room temperature. The reaction solution was extracted by methylene dichloride (MC) and water, and an organic layer was recovered. The organic layer was concentrated under reduced pressure and recrystallized with ethyl acetate (EA) to obtain the intermediate 1 (10.5 g).

22
(2) Intermediate 2

[Reaction Formula 1-2]

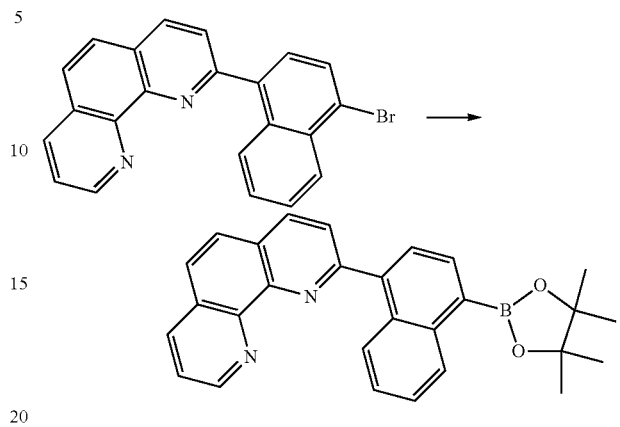

The intermediate (10 g, 0.075 mol), bis(pinacolato)diboron (7.9 g, 0.04 mol), [1,1'-Bis(diphenylphosphino)ferrocene]dichloropalladium(II) (1.1 g, 0.2 mmol), KOAc(potassium acetate) (9.2 g, 0.09 mol) and 1,4-dioxane (200 ml) were put into the round-bottom flask and heated. The mixture was refluxed and stirred for 12 hrs. The reaction solution was cooled to room temperature and filtered by celite. The celite was washed by chloroform ($CHCl_3$). The residual solution was concentrated under reduced pressure and recrystallized with ethyl acetate (EA) to obtain the intermediate 2 (7.9 g).

(3) Intermediate 3

[Reaction Formula 1-3]

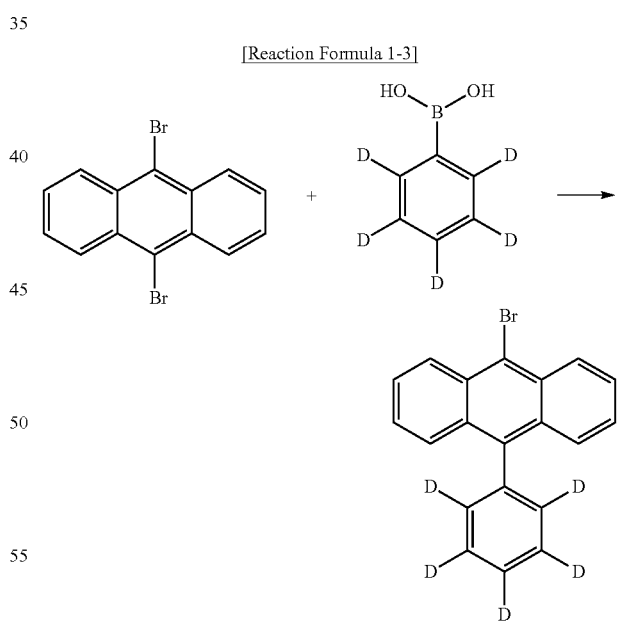

9,10-dibromoanthracene (10 g, 0.03 mol), phenyl-d5-boronicacid (3.8 g, 0.03 mol), tetrakis(triphenylphosphine) palladium(0) (1.4 g, 0.1 mmol), toluene (200 ml) and 4M $K_2CO_3$ (potassium carbonate, 15 ml) were put into the round-bottom flask, and the mixture was refluxed and stirred for 12 hrs. After completion of reaction, the reaction solution was filtered to obtain a crude product. The crude product was dissolved in methylenechloride. The mixture was dried by MgSO$_4$ and concentrated under reduced pressure. The concentration solution was column-separated by using a mixed solution of MC and hexane (volume ratio=10:1) to obtain the intermediate 3 (7 g).

(4) Compound D10

[Reaction Formula 1-4]

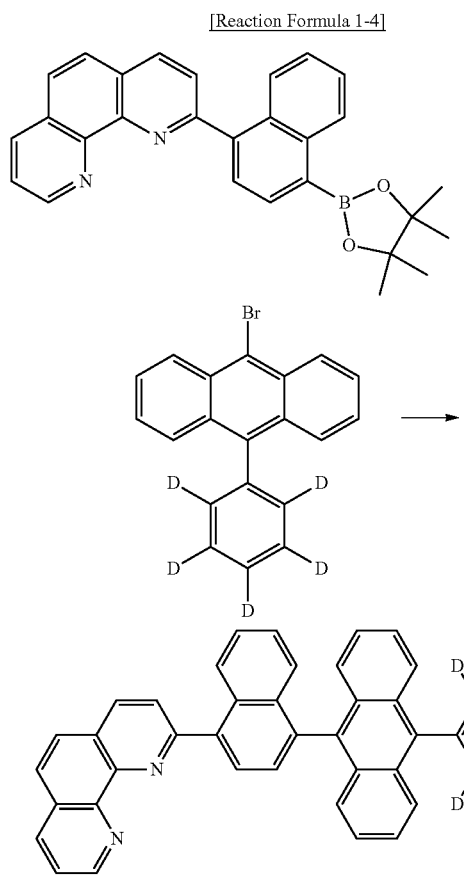

The intermediate 2 (5 g, 0.01 mol), the intermediate 3 (2.9 g, 0.01 mol), tetrakis(triphenylphosphine)palladium(0) (0.5 g, 0.05 mmol), toluene (100 ml), EtOH(ethanol) (20 ml) and 4M K$_2$CO$_3$ (potassium carbonate, 8 ml) were put into the round-bottom flask. The mixture was refluxed and stirred for 12 hrs. After completion of reaction, the reaction solution was filtered to obtain a crude product. The crude product was column-separated by using a solution of CHCl$_3$ to obtain the compound D10 (4.3 g).

2. Synthesis of Compound D13

(1) Intermediate 4

[Reaction Formula 2-1]

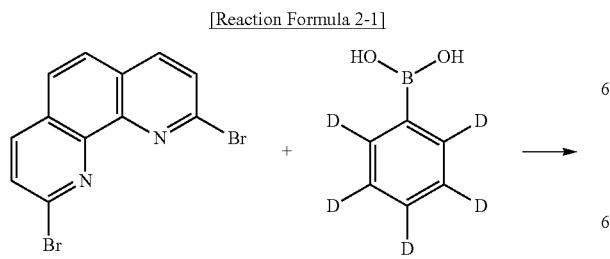

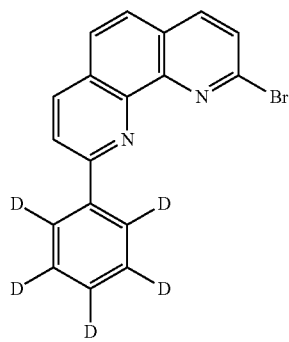

2,9-dibromo-1,10-phenanthroline (10 g, 0.03 mol), phenyl-d5-boronicacid (3.8 g, 0.03 mol), tetrakis(triphenylphosphine)palladium(0) (1.4 g, 0.1 mmol), toluene (200 ml), EtOH (50 ml), 4M K$_2$CO$_3$ (potassium carbonate, 15 ml) were put into the round-bottom flask, and the mixture was refluxed and stirred for 12 hrs. After completion of reaction, the reaction solution was filtered to obtain a crude product. The crude product was dissolved in methylenechloride. The mixture was dried by MgSO$_4$ and concentrated under reduced pressure. The concentration solution was column-separated by using a solution of CHCl$_3$ to obtain the intermediate 4 (8.3 g).

(2) Compound D13

[Reaction Formula 2-2]

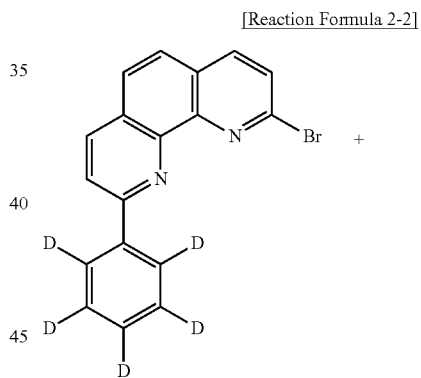

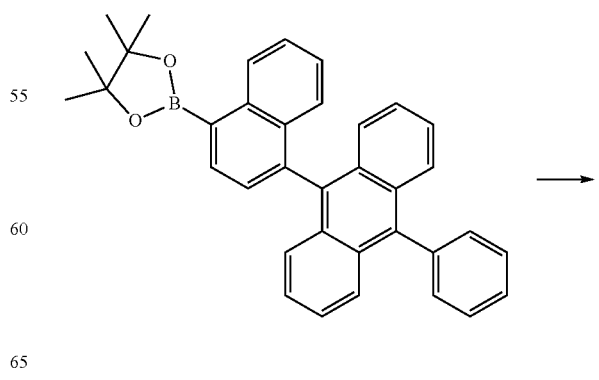

-continued

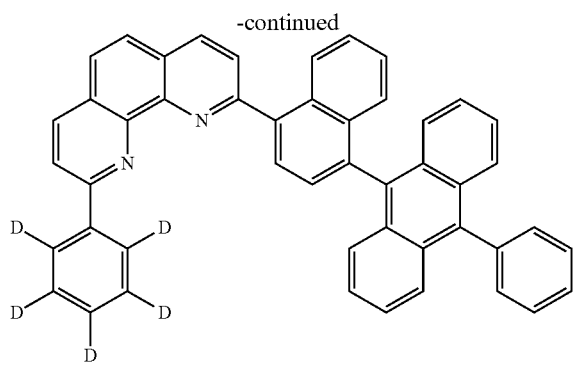

The intermediate 4 (5 g, 0.015 mol), 4,4,5,5-tetramethyl-2-(1-(10-phenylanthracen-9-yl)naphthalen-4-yl)-1,3,2-dioxaborolane (8.2 g, 0.016 mol), tetrakis(triphenylphosphine)palladium(0) (0.7 g, 0.05 mmol), toluene (100 ml), EtOH (50 ml), 4M $K_2CO_3$ (10 ml) were put into the round-bottom flask. The mixture was refluxed and stirred for 12 hrs. After completion of reaction, the reaction solution was filtered to obtain a crude product. The crude product was dissolved in methylenechloride. The mixture was dried by $MgSO_4$ and concentrated under reduced pressure. The concentration solution was column-separated by using a solution of $CHCl_3$ to obtain the compound D13 (4.3 g).

3. Synthesis of Compound D16

[Reaction Formula 3]

2-bromo-d6-1,10-phenanthroline (5 g, 0.02 mol), 4,4,5,5-tetramethyl-2-(1-(10-phenyl anthracen-9-yl)naphthalen-4-yl)-1,3,2-dioxaborolane (10.5 g, 0.02 mol), tetrakis(triphenylphosphine)palladium(0) (0.9 g, 0.1 mmol), toluene (100 ml), EtOH (40 ml), 4M $K_2CO_3$ (15 ml) were put into the round-bottom flask. The mixture was refluxed and stirred for 12 hrs. After completion of reaction, the reaction solution was filtered to obtain a crude product. The crude product was dissolved in methylenechloride. The mixture was dried by $MgSO_4$ and concentrated under reduced pressure. The concentration solution was column-separated by using a solution of $CHCl_3$ to obtain the compound D16 (4.1 g).

4. Synthesis of Compound D18

[Reaction Formula 4]

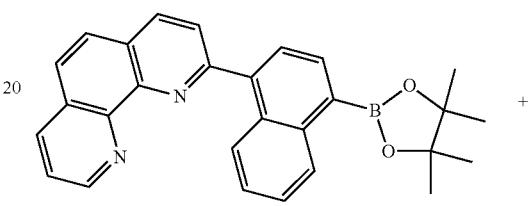

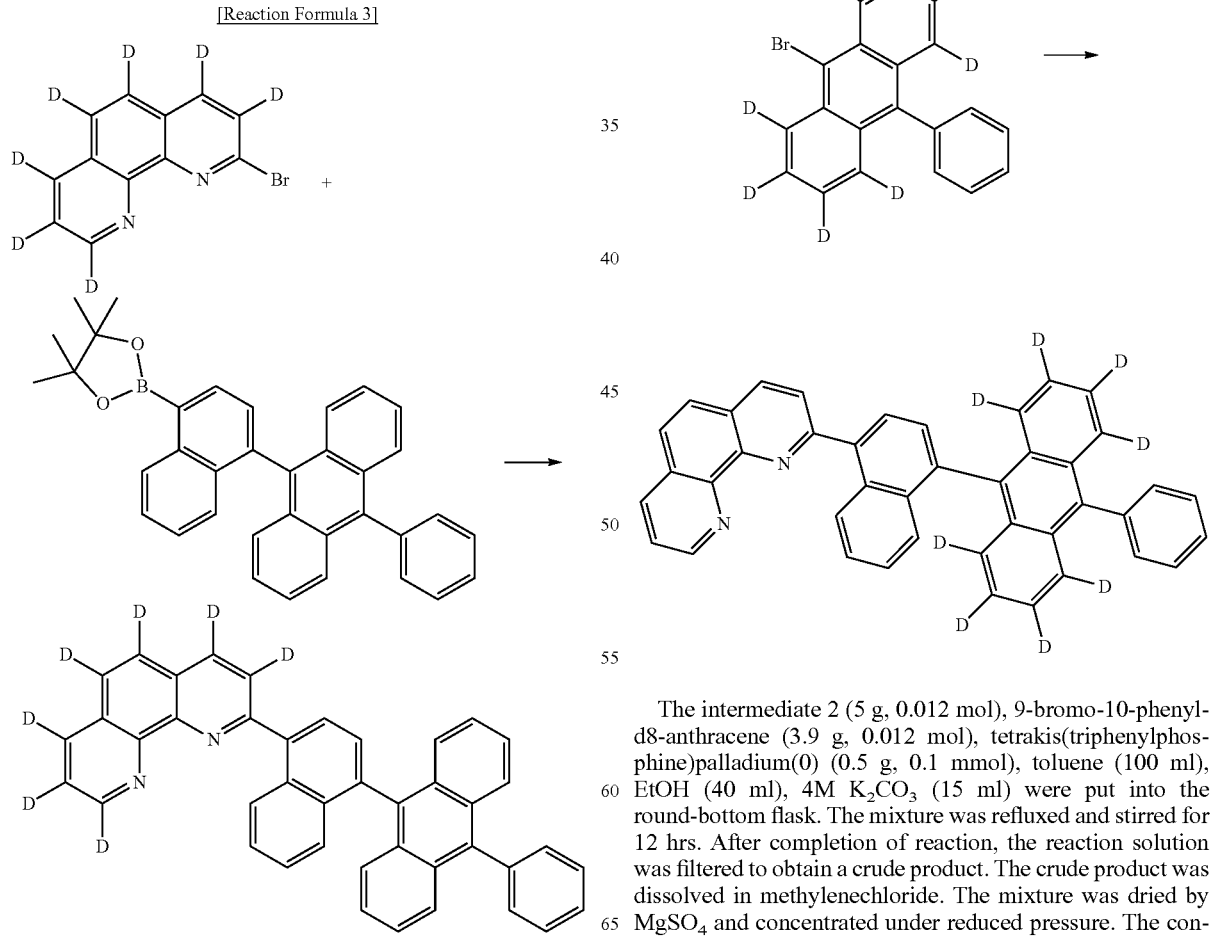

The intermediate 2 (5 g, 0.012 mol), 9-bromo-10-phenyl-d8-anthracene (3.9 g, 0.012 mol), tetrakis(triphenylphosphine)palladium(0) (0.5 g, 0.1 mmol), toluene (100 ml), EtOH (40 ml), 4M $K_2CO_3$ (15 ml) were put into the round-bottom flask. The mixture was refluxed and stirred for 12 hrs. After completion of reaction, the reaction solution was filtered to obtain a crude product. The crude product was dissolved in methylenechloride. The mixture was dried by $MgSO_4$ and concentrated under reduced pressure. The concentration solution was column-separated by using a solution of $CHCl_3$ to obtain the compound D18 (5 g).

5. Synthesis of Compound D19

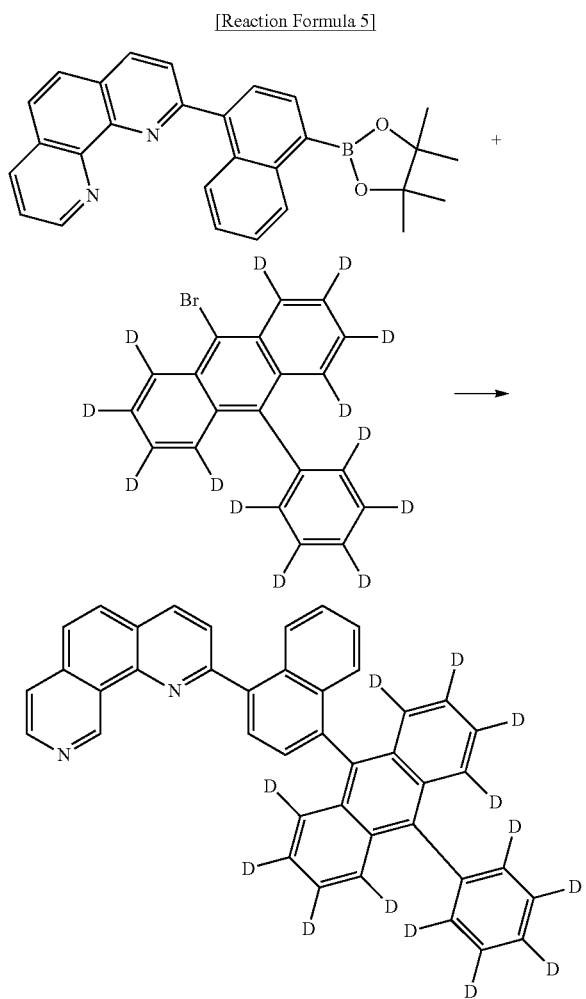

[Reaction Formula 5]

9-bromo-10-d5-phenyl-d8-anthracene was used instead of 9-bromo-10-phenyl-d6-anthracene in the synthesis of the compound D18 to obtain the compound D19 (4.8 g).

6. Synthesis of Compound D20

[Reaction Formula 6]

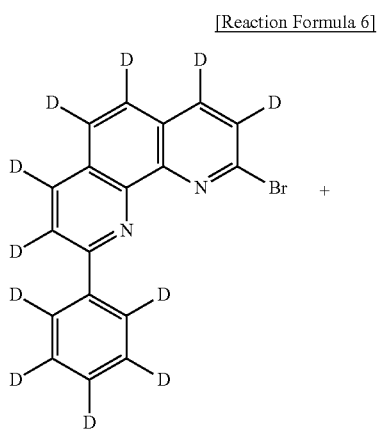

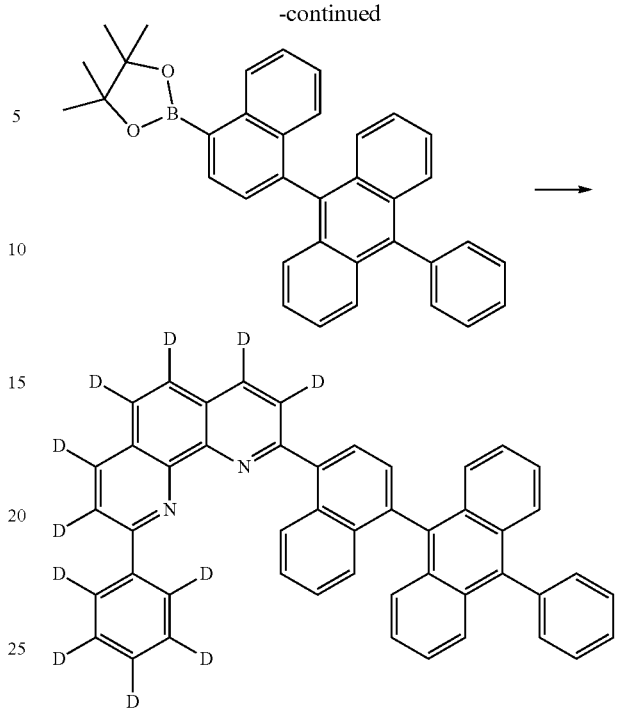

2-d5phenyl-9-bromo-d6-1,10-phenanthroline was used instead of the intermediate 4 in the synthesis of the compound D13 to obtain the compound D20 (4.8 g).

Referring to FIG. 2, in the organic emitting layer 170, the hole auxiliary layer may include a hole injection layer (HIL) being adjacent to the first electrode 160 and a hole transporting layer (HTL) being adjacent to the EML. The electron auxiliary layer may include an electron transporting layer (ETL) being adjacent to the EML and an electron injection layer (EIL) being adjacent to the second electrode 180.

The organic compound of the present disclosure may be included in the HTL and enhances an electron transporting property from the second electrode 180 into the EML. As a result, the emitting efficiency and the lifespan of the OLED D and the organic light emitting display device 100 are improved.

Although not shown, an encapsulation film may be formed on the second electrode 180 to prevent penetration of moisture into the OLED D. The encapsulation film may include a first inorganic insulating layer, an organic insulating layer and a second inorganic insulating layer sequentially stacked, but it is not limited thereto.

In addition, a polarization plate for reducing an ambient light reflection may be disposed on or over the encapsulation film in the top-emission type OLED D. For example, the polarization plate may be a circular polarization plate.

FIG. 3 is a schematic cross-sectional view illustrating an OLED of the present disclosure.

As illustrated in FIG. 3, the OLED D includes the first and second electrodes 160 and 180, which face each other, and the organic emitting layer 170 therebetween. The organic emitting layer 170 includes a first emitting part ST1, a second emitting part ST2 and a charge generation layer (CGL) 230.

The first electrode 160 may be formed of a conductive material having a relatively high work function to serve as an anode injecting a hole. For example, the first electrode 160 may be formed of one of ITO, IZO and ZnO. The second electrode 180 may be formed of a conductive material having a relatively low work function to serve as a cathode injecting an electrode. For example, the second electrode 180 may be formed of Al, Mg and Al—Mg alloy.

The CGL 230 is positioned between the first and second emitting parts ST1 and ST2, and the first emitting part ST1, the CGL 230 and the second emitting part ST2 are sequentially stacked on the first electrode 160. Namely, the first emitting part ST1 is positioned between the first electrode 160 and the CGL 230, and the second emitting part ST2 is positioned between the second electrode 180 and the CGL 230.

The first emitting part ST1 may include an HIL 212, a first HTL 214, a first EML 216 and a first ETL 218 sequentially stacked on the first electrode 160. Namely, the HIL 212 and the first HTL 214 are positioned between the first electrode 160 and the first EML 216, and the HIL 212 is positioned between the first electrode 160 and the first HTL 214. The first ETL 218 is positioned between the first EML 216 and the CGL 230. The HIL 212 and the first HTL 214 may be a first hole auxiliary layer, and the first ETL may be a first electron auxiliary layer.

The HIL 212 enhances the hole injection from the first electrode 160 into the first EML 216. The HIL 212 may include at least one selected from the group consisting of HATCN (hexaazatriphenylenehexacarbonitrile, Formula 8), CuPc (cupper phthalocyanine), PEDOT (poly(3,4)-ethylenedioxythiophene) and PANI (polyaniline), but it is not limited thereto.

Formula 8

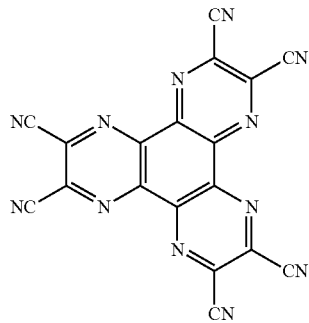

The HIL 212 may have a thickness of about 1 to 150 nm. When the thickness of the HIL 212 is 1 nm or more, the hole injection property may be improved. When the thickness of the HIL 212 is 150 nm or less, a problem of the increase in the driving voltage by an increase in the thickness of the HIL 212 may be prevented. The HIL 212 may be omitted depending on the structure or characteristics of the OLED.

The first HTL 214 enhances the hole transport into the first EML 216. The first HTL 214 may include at least one selected from the group consisting of NPD (N,N'-bis(naphthalen-1-yl)-N,N'-bis(phenyl)-2,2'-dimethylbenzidine, Formula 9), TPD (N,N'-bis-(3-methylphenyl)-N,N'-bis-(phenyl)-benzidine), spiro-TAD (2,2',7,7'-tetrakis(N,N-diphenylamino)-9,9'-spirofluorene) and MTDATA (4,4',4''-Tris(N-3-methylphenyl-N-phenylamino)-triphenylamine), but it is not limited thereto.

Formula 9

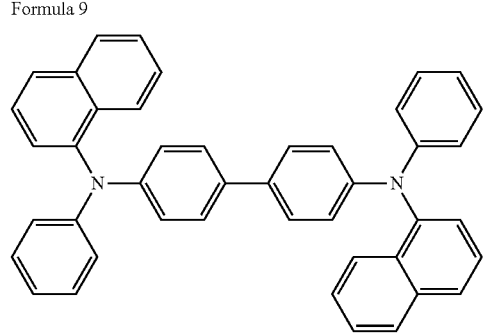 [SMILES: c1ccc(N(c2ccc(-c3ccc(N(c4ccccc4)c4cccc5ccccc45)cc3)cc2)c2cccc3ccccc23)cc1]

The first HTL 214 may have a thickness of about 1 to 150 nm. When the thickness of the first HTL 214 is 1 nm or more, the hole transporting property may be improved. When the thickness of the first HTL 214 is 150 nm or less, a problem of the increase in the driving voltage by an increase in the thickness of the first HTL 214 may be prevented.

The first EML 216 may be a blue EML. Alternatively, the first EML 216 may be a red EML, a green EML or a yellow EML. When the first EML 216 is the blue EML, the first EML 216 may include a host and a blue dopant. Each of the host and the blue dopant may be a fluorescent compound, a phosphorescent compound or a delayed fluorescent compound. For example, the first EML 216 may include a host of Formula 10 and a dopant of Formula 11.

Formula 10

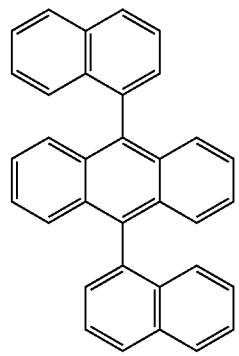

Formula 11

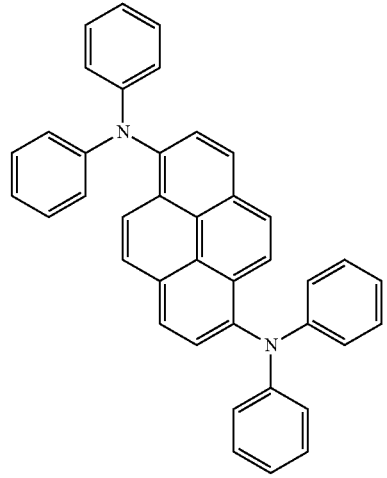

The first ETL 218 enhances the electron transport into the first EML 216. The first ETL 218 may include at least one selected from the group consisting of the organic compound of the present disclosure, a compound of Formula 12, Alq$_3$ (tris(8-hydroxy-quinolinato)aluminum), PBD (2-(4-biphenyl)-5-(4-tertbutylphenyl)-1,3,4-oxadiazole), TAZ (3-(4-biphenyl)-4-phenyl-5-tertbutylphenyl-1,2,4-triazole) and BAlq (Bis(2-methyl-8-quinolinolate)-4-(phenylphenolato) aluminum), but it is not limited thereto.

Formula 12

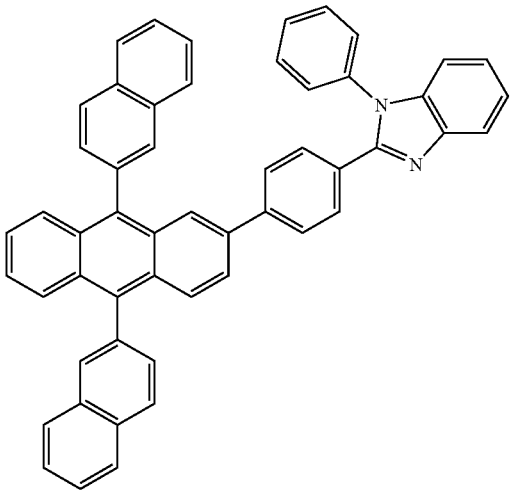

The first ETL 218 may have a thickness of about 1 to 150 nm. When the thickness of the first ETL 218 is 1 nm or more, the decrease of the electron transporting property may be prevented. When the thickness of the first ETL 218 is 150 nm or less, a problem of the increase in the driving voltage by an increase in the thickness of the first ETL 218 may be prevented.

The second emitting part ST2 may include a second HTL 222, a second EML224, a second ETL 226 and an EIL 228. The second HTL 222 is positioned between the CGL 230 and the second EML224. The second ETL 226 is positioned between the second EML224 and the second electrode 180, and the EIL 228 is positioned between the second ETL 226 and the second electrode 180. The second ETL 222 may be a second hole auxiliary layer, and the second ETL 226 and the EIL 228 may be a second electron auxiliary layer.

The second HTL 222 and the second ETL 226 may have same structure or material as the first HTL 214 and the first ETL 218 of the first emitting part ST1, respectively. Alternatively, the second HTL 222 and the second ETL 226 may have different structure or material from the first HTL 214 and the first ETL 218 of the first emitting part ST1, respectively. The EIL 228 may be omitted depending on the structure or characteristics of the OLED.

The second EML 224 may be a red EML, a green EML, a blue EML or a yellow-green EML. For example, the first EML 216 is a blue EML, and the second EML 224 is a yellow-green EML. Alternatively, the first EML 216 is a yellow-green EML, and the second EML 224 is a blue EML. Namely, the blue light may be emitted from one of the first and second emitting parts ST1 and ST2, i.e., the first and second EMLs 216 and 224, and the yellow-green light may be emitted from the other one of the first and second emitting parts ST1 and ST2, i.e., the first and second EMLs 216 and 224.

When the second EML 224 emits the yellow-green light, the second EML 224 may include a first host of a biscarbazole-based compound, a second host of a triazine-based compound and a dopant of an iridium complex.

The EIL 228 enhances the electron injection and may include at least one of Alq$_3$ (tris(8-hydroxy-quinolinato) aluminum), PBD (2-(4-biphenyl)-5-(4-tertbutylphenyl)-1,3, 4-oxadiazole), TAZ (3-(4-biphenyl)-4-phenyl-5-tertbutylphenyl-1,2,4-triazole) and BAlq (Bis(2-methyl-8-quinolinolate)-4-(phenylphenolato)aluminum), but it is not limited thereto.

Alternatively, the EIL 228 may include a metallic material. For example, the EIL 228 may include at least one selected from the group consisting of LiQ, LiF, NaF, KF, RbF, CsF, FrF, BeF$_2$, MgF$_2$, CaF$_2$, SrF$_2$, BaF$_2$ and RaF$_2$, but it is not limited thereto.

The EIL 228 may have a thickness of about 1 to 50 nm. When the thickness of the EIL 228 is 1 nm or more, the decrease of the electron injection property may be prevented. When the thickness of the EIL 228 is 50 nm or less, a problem of the increase in the driving voltage by an increase in the thickness of the EIL 222 may be prevented.

The CGL 230 is positioned between the first emitting part ST1 and the second emitting part ST2. Namely, the first and second emitting parts ST1 and ST2 are connected through the CGL 230. The CGL 230 may be a P-N junction CGL of an N-type CGL 230N and a P-type CGL 230P.

The N-type CGL 230N is positioned between the first ETL 218 and the second HTL 222, and the P-type CGL 230P is positioned between the N-type CGL 230N and the second HTL 222.

The CGL 230 generates charges, and a hole and an electron are separated and provided into the first and second emitting parts ST1 and ST2.

Namely, the N-type CGL 230N provides the electron into the first ETL 218 of the first emitting part ST1, and the first ETL 218 provides the electron into the first EML 216 being adjacent to the first electrode 160. The P-type CGL 230P provides the hole into the second HTL 222 of the second emitting part ST2, and the second ETL 222 provides the hole into the second EML 224 being adjacent to the second electrode 180. Accordingly, the emitting efficiency of the OLED D, which includes a plurality of EMLs, is improved, and the driving voltage of the OLED D is reduced.

The P-type CGL 230P includes a material of the HIL 212, a material of the first ETL 214 or a material of the second HTL 222. For example, the P-type CGL 230P may include HATCN.

The N-type CGL 230N include the organic compound of the present disclosure such that the electron injection and/or transport property into the first ETL 218 is improved. As a result, the emitting efficiency and the lifespan of the OLED D are improved.

[OLED]

In the vacuum chamber, on an ITO layer, i.e., an anode, an HIL (HATCN), a first HTL (a compound of Formula 9), a first EML, a first ETL (a compound of Formula 12), an N-type CGL, a P-type CGL (HATCN), a second HTL (a compound of Formula 9), a second EML, a second ETL (a compound of Formula 12), an EIL (LiF) and a cathode (AL) are sequentially stacked to form an OLED.

In this instance, the first EML is formed using a compound of Formula 10 as a host and a compound of Formula 11 as a dopant, and the second EML is formed using a biscarbazole-based compound as a first host, a triazine-based compound as a second host and an iridium complex as a dopant.

(1) Comparative Example

A compound of Formula 13 is used to form the N-type CGL.

(2) Example 1

The compound D10 in Formula 7 is used to form the N-type CGL.

(3) Example 2

The compound D13 in Formula 7 is used to form the N-type CGL.

(4) Example 3

The compound D16 in Formula 7 is used to form the N-type CGL.

(5) Example 4

The compound D18 in Formula 7 is used to form the N-type CGL.

(6) Example 5

The compound D19 in Formula 7 is used to form the N-type CGL.

(7) Example 6

The compound D20 in Formula 7 is used to form the N-type CGL.

Formula 13

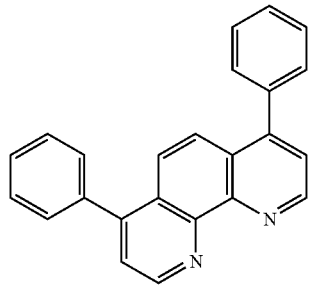

The emitting properties, i.e., the driving voltage, the emitting efficiency and the lifespan, of the OLED in Comparative Example and Examples 1 to 6 are measured and listed in Table 1.

TABLE 1

| N-CGL | Voltage (ΔV) | Emitting efficiency (sample/Ref, %) | Lifespan (sample/Ref, %) |
|---|---|---|---|
| Formula 13 | 0 | 100% | 100% |
| D10 | 0 | 100% | 104% |
| D13 | −0.2 | 105% | 135% |
| D16 | −0.1 | 102% | 113% |
| D18 | 0 | 102% | 108% |
| D19 | 0 | 103% | 111% |
| D20 | −0.2 | 105% | 138% |

As shown in Table 1, in comparison to the OLED using the compound of Formula 13 to the N-type CGL, the emitting efficiency and the lifespan of the OLED using the organic compound of the present disclosure to the N-type CGL are improved.

In addition, in comparison to the OLED of Examples 1, 4 and 5 using the organic compounds D10, D18 and D19, in which the anthracene moiety or the substituent of the anthracene moiety is deuterated, the emitting efficiency and the lifespan of the OLED using the organic compounds D13, D16 and D20, in which the phenanthroline moiety or the substituent of the phenanthroline moiety is deuterated, are significantly improved.

FIG. 4 is a schematic cross-sectional view illustrating an OLED of the present disclosure.

As illustrated in FIG. 4, the OLED D includes the first and second electrodes 160 and 180, which face each other, and the organic emitting layer 170 therebetween. The organic emitting layer 170 includes first to third emitting parts ST1, ST2 and ST3 and first and second CGLs 330 and 350. Alternatively, four or more emitting parts and three or more CGLs may be disposed between the first and second electrodes 160 and 180.

As mentioned above, the first electrode 160 may be formed of a conductive material having a relatively high work function to serve as an anode injecting a hole. For example, the first electrode 160 may be formed of one of ITO, IZO and ZnO. The second electrode 180 may be formed of a conductive material having a relatively low work function to serve as a cathode injecting an electrode. For example, the second electrode 180 may be formed of Al, Mg and Al—Mg alloy.

The first CGL 330 is positioned between the first and second emitting parts ST1 and ST2, and the second CGL 350 is positioned between the second and third emitting parts ST2 and ST3. The first emitting part ST1, the first CGL 330, the second emitting part ST2, the second CGL 350 and the third emitting part ST3 are sequentially stacked on the first electrode 160. Namely, the first emitting part ST1 is positioned between the first electrode 160 and the first CGL 330, the second emitting part ST2 is positioned between the first and second CGLs 330 and 350, and the third emitting part ST3 is positioned between the second electrode 180 and the second CGL 350.

The first emitting part ST1 includes an HIL 312, a first HTL 314, a first EML 316 and a first ETL 318 sequentially stacked on the first electrode 160. Namely, the HIL 312 and the first HTL 314 is positioned between the first electrode 160 and the first EML 316, and the HIL 312 is positioned between the first electrode 160 and the first HTL 314. The first ETL 318 is positioned between the first EML 316 and the first CGL 330.

The HIL 312, the first HTL 314, the first EML 316 and the first ETL 318 may have the same properties (characteristics) as the HIL 212, the first HTL 214, the first EML 216 and the first ETL 218 explained with FIG. 3. For example, the first ETL 318, which may be a first electron auxiliary layer, may include the organic compound of the present disclosure. In addition, the first EML 316 may be a blue EML.

The second emitting part ST2 includes a second HTL 322, a second EML 324 and a second ETL 326. The second HTL 322 is positioned between the first CGL 330 and the second EML 324, and the second ETL 326 is positioned between the second EML 324 and the second CGL 350.

The second HTL 322 may be a second hole auxiliary layer, and the second ETL 326 may be a second electron auxiliary layer. For example, the second ETL 326 may include the organic compound of the present disclosure. The second EML 324 may be a yellow-green EML.

The third emitting part ST3 includes a third HTL 342, a third EML 344, a third ETL 346 and an EIL 348. The third HTL 342 is positioned between the second CGL 350 and the third EML 344, and the third ETL 346 is positioned between the third EML 344 and the second electrode 180. The EIL 348 is positioned between the third ETL 346 and the second electrode 180.

The third HTL 342 may be a third hole auxiliary layer, and the third ETL 346 and the EIL 348 may be a third electron auxiliary layer. For example, the third ETL 346 may include the organic compound of the present disclosure. The third EML 344 may be a blue EML.

The first CGL 330 is positioned between the first emitting part ST1 and the second emitting part ST2, and the second CGL 350 is positioned between the second emitting part ST2 and the third emitting part ST3. The first CGL 330 may be a P-N junction CGL of an N-type CGL 330N and a P-type CGL 330P, and the second CGL 350 may be a P-N junction CGL of an N-type CGL 350N and a P-type CGL 350P.

In the first CGL 330, the N-type CGL 330N is positioned between the first ETL 318 and the second HTL 322, and the P-type CGL 330P is positioned between the N-type CGL 330N and the second HTL 322.

In the second CGL 350, the N-type CGL 350N is positioned between the second ETL 326 and the third HTL 342, and the P-type CGL 350P is positioned between the N-type CGL 350N and the third HTL 342.

Each of the first and second CGL 330 and 350 generates charges, and a hole and an electron are separated and provided into the first to third emitting parts ST1, ST2 and ST3.

Namely, in the first CGL 330, the N-type CGL 330N provides the electron into the first ETL 318 of the first emitting part ST1, and the P-type CGL 330P provides the hole into the second HTL 322 of the second emitting part ST2.

In the second CGL 350, the N-type CGL 350N provides the electron into the second ETL 326 of the second emitting part ST2, and the P-type CGL 350P provides the hole into the third HTL 342 of the third emitting part ST3.

Each of the P-type CGL 330P of the first CGL 330 and the P-type CGL 350P of the second CGL 350 includes the same material as one of a material of the HIL 312, a material of the first HTL 312, a material of the second HTL 322 and a material of the third HTL 342. For example, each of the P-type CGL 330P of the first CGL 330 and the P-type CGL 350P of the second CGL 350 may include (be formed of) HATCN.

Each of the N-type CGL 330N of the first CGL 330 and the N-type CGL 350N of the second CGL 350 includes the organic compound of the present disclosure. As a result, the electron providing (transporting) property into the first ETL 318 and/or the second ETL 326 is improved, and the emitting efficiency and the lifespan of the OLED D are improved.

FIG. 5 is a schematic cross-sectional view illustrating an organic light emitting display device according to the present disclosure.

As shown in FIG. 5, the organic light emitting display device 400 includes a substrate 410, the OLED D positioned above the substrate 410, a driving TFT Td, which is positioned between the substrate 410 and the OLED D and connected to the OLED D, and a color filter 430 between the substrate 410 and the OLED D.

The substrate 410 may be a glass substrate or a plastic substrate. For example, the substrate 410 may be formed of polyimide.

The substrate 410 may include a red pixel region RP, a green pixel region GP and a blue pixel region BP, and the driving TFT Td may be positioned in each of the red, green and blue pixel regions RP, GP and BP. The substrate 410 may further include a white pixel region (not shown), and the driving TFT Td may be further positioned in the white pixel region.

For example, the driving TFT Td may include a semiconductor layer formed on the substrate 410, a gate electrode, which is positioned over and overlap the semiconductor layer, and a source electrode and a drain electrode, which are positioned over the gate electrode and respectively connected to both ends of the semiconductor layer.

A first insulating layer 420 is formed on the driving TFT Td, and a color filter 430 is formed on the first insulating layer 420. The color filter 430 includes a red color filter pattern 430a corresponding to the red pixel region RP, a green color filter pattern 430b corresponding to the green pixel region GP and a blue color filter pattern 430c corresponding to the blue pixel region BP.

A second insulating layer 440 is formed on the color filter 430, and a contact hole 422 exposing an electrode, e.g., the drain electrode, of the driving TFT Td is formed through the first and second insulating layers 420 and 440.

Namely, the color filter 430 is positioned between the first and second insulating layers 420 and 440. When the white pixel region is further included, there is no color filter in the white pixel region such that the first and second insulating layers 420 and 440 in the white pixel region may entirely contact each other.

A first electrode 160 connected to the driving TFT Td through the contact hole 422 is formed on the second insulating layer 440 to be separate in the red, green and blue pixel regions RP, GP and BP. The first electrode 160 may be an anode and may be formed of a conductive material having a relatively high work function. For example, the first electrode 160 may be formed of one of ITO, IZO and ZnO.

A bank 460 covering an edge of the first electrode 160 is formed on the second insulating layer 440. The bank 460 exposes a center of the first electrode 160 in the red, green and blue pixel regions RP, GP and BP.

An organic emitting layer 170 is formed on the first electrode 160. The organic emitting layer 170 emits white light. The organic emitting layers 170 in the red, green and blue pixel regions RP, GP and BP are integrated as one-body in a display area.

A second electrode 180 is formed over the substrate 410 including the organic emitting layer 170. The second electrode 180 covers an entire surface of the display area including the red, green and blue pixel regions RP, GP and BP and may be formed of a conductive material having a relatively low work function to serve as a cathode. For example, the second electrode 180 may be formed of aluminum (Al), magnesium (Mg) or Al—Mg alloy.

The first electrode 160, the organic emitting layer 170 and the second electrode 180 constitute the OLED D.

Although not shown, an encapsulation film may be formed on the second electrode 180 to prevent penetration of moisture into the OLED D. The encapsulation film may include a first inorganic insulating layer, an organic insulating layer and a second inorganic insulating layer sequentially stacked, but it is not limited thereto. In addition, a polarization plate for reducing an ambient light reflection may be disposed under the substrate 410. For example, the polarization plate may be a circular polarization plate.

Moreover, a cover window may be attached to the substrate 410 or the polarization plate. The substrate 410 and the cover window has a flexible property such that a flexible display device may be provided.

The organic light emitting display device 400 is a bottom-emission type. Namely, the light from the organic emitting layer 170 passes through the first electrode 160, the color filter 430 and the substrate 410 to display an image.

Namely, the first electrode 160 serves as a transparent electrode, and the second electrode 180 serves as a reflective electrode. The light from the organic emitting layer 170 may directly pass through the first electrode 160 or indirectly pass through the first electrode 160 after being reflected by the second electrode 180.

In FIG. 5, the color filter 430 is disposed between the first and second insulating layers 420 and 440. Alternatively, a position of the color filter 430 is not limited between the OLED D and the substrate 410. For example, the color filter 430 may be positioned between the substrate 410 and the first insulating layer 420. In this instance, the second insulating layer 440 may be omitted.

The white light from the OLED D passes through the color filter 430, the organic light emitting display device 400 can provide a color image.

As explained with FIGS. 3 and 4, the OLED D is a white OLED having a multi-stack structure, and at least one of the ETL and the N-type CGL includes the organic compound of the present disclosure. Accordingly, the emitting efficiency and the lifespan of the organic light emitting display device are improved.

FIG. 6 is a schematic cross-sectional view illustrating an organic light emitting display device according to the present disclosure.

As shown in FIG. 6, the organic light emitting display device 500 includes a first substrate 510, a second substrate 570 facing the first substrate 510, the OLED D positioned above the first substrate 510, a driving TFT Td, which is positioned between the first substrate 510 and the OLED D and connected to the OLED D, and a color filter 530 between the second substrate 570 and the OLED D.

Each of the first and second substrates 510 and 570 may be a glass substrate or a plastic substrate. For example, each of the first and second substrates 510 and 570 may be formed of polyimide.

The first substrate 510 may include a red pixel region RP, a green pixel region GP and a blue pixel region BP, and the driving TFT Td may be positioned in each of the red, green and blue pixel regions RP, GP and BP. The first substrate 510 may further include a white pixel region (not shown), and the driving TFT Td may be further positioned in the white pixel region.

For example, the driving TFT Td may include a semiconductor layer formed on the first substrate 510, a gate electrode, which is positioned over and overlap the semiconductor layer, and a source electrode and a drain electrode, which are positioned over the gate electrode and respectively connected to both ends of the semiconductor layer.

An insulating layer 520 is formed on the driving TFT Td, and a contact hole 522 exposing an electrode, e.g., the drain electrode, of the driving TFT Td is formed through the insulating layers 520.

A first electrode 160 connected to the driving TFT Td through the contact hole 522 is formed on the insulating layer 520 to be separate in the red, green and blue pixel regions RP, GP and BP. The first electrode 160 may be an anode and may be formed of a conductive material having a relatively high work function. The first electrode 160 includes a transparent electrode layer formed of the transparent conductive material, e.g., ITO, IZO or ZnO, and a reflective electrode layer (or a reflective layer). For example, the first electrode 160 may have a triple-layered structure including lower and upper layers of ITO or IZO and an intermediate layer of aluminum-palladium-copper (AFC) ally or Ag.

A bank 560 covering an edge of the first electrode 160 is formed on the insulating layer 520. The bank 560 exposes a center of the first electrode 160 in the red, green and blue pixel regions RP, GP and BP.

An organic emitting layer 170 is formed on the first electrode 160. The organic emitting layer 170 emits white light. The organic emitting layers 170 in the red, green and blue pixel regions RP, GP and BP are integrated as one-body in a display area.

A second electrode 180 is formed over the first substrate 510 including the organic emitting layer 170. The second electrode 180 covers an entire surface of the display area including the red, green and blue pixel regions RP, GP and BP and may be formed of a conductive material having a relatively low work function to serve as a cathode. For example, the second electrode 180 may be formed of aluminum (Al), magnesium (Mg) or Al—Mg alloy. The second electrode 180 has a relatively thin profile such that the light passes through the second electrode 180.

The first electrode 160, the organic emitting layer 170 and the second electrode 180 constitute the OLED D.

A color filter 530 is formed over the OLED D. Namely, the color filter 530 is positioned between the OLED D and the second electrode 570. The color filter 530 includes a red color filter pattern 530a corresponding to the red pixel region RP, a green color filter pattern 530b corresponding to the green pixel region GP and a blue color filter pattern 530c corresponding to the blue pixel region BP.

Although not shown, a polarization plate for reducing an ambient light reflection may be disposed an outer side of the second substrate 570. For example, the polarization plate may be a circular polarization plate.

The organic light emitting display device 500 is a top-emission type. Namely, the light from the organic emitting layer 170 passes through the second electrode 180, the color filter 530 and the second substrate 570 to display an image.

Namely, the first electrode 160 serves as a reflective electrode, and the second electrode 180 serves as a transparent electrode (semi-transparent electrode). The light from the organic emitting layer 170 may directly pass through the second electrode electrode 180 or indirectly pass through the second electrode 180 after being reflected by the first electrode 160.

The white light from the OLED D passes through the color filter 530, the organic light emitting display device 500 can provide a color image.

As explained with FIGS. 3 and 4, the OLED D is a white OLED having a multi-stack structure, and at least one of the ETL and the N-type CGL includes the organic compound of the present disclosure. Accordingly, the emitting efficiency and the lifespan of the organic light emitting display device are improved.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of patents, patent application publications, patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound of Formula 1:

Formula 1 wherein $L_1$ is selected from a C6 to C30 arylene group, and $L_2$ is selected from a C6 to C30 aryl group, a C6 to C30 arylene group, a C5 to C30 heteroaryl group and a C5 to C30 heteroarylene group, and each of $R_1$ and $R_2$ is independently selected from a C1 to C10 alkyl group, a C6 to C30 aryl group and a C5 to C30 heteroaryl group, wherein each of c and d is independently 0 (zero) or a positive integer, and wherein at least one of n1 and n4 is the positive integer, and n2, n5 and n6 are 0.

2. The organic compound according to claim 1, wherein $L_1$ is selected from phenylene and naphthylene, and $L_2$ is selected from phenyl, phenylene, naphthyl, naphthylene, pyridyl and pyridylene, and wherein $R_1$ is selected from methyl, phenyl, naphthyl, pyridyl and isoquinolinyl, and $R_2$ is selected from pyridyl and pyrimidyl.

3. The organic compound according to claim 1, wherein the organic compound of Formula 1 is one of compounds:

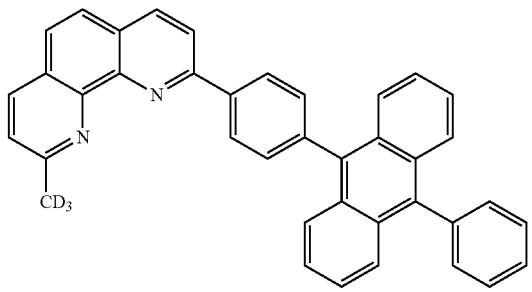

D4

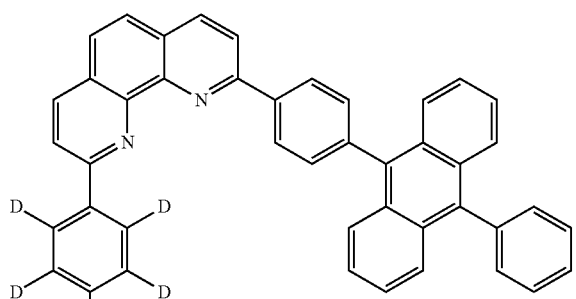

D7

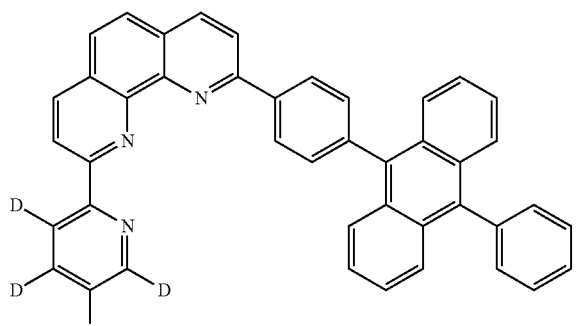

D8

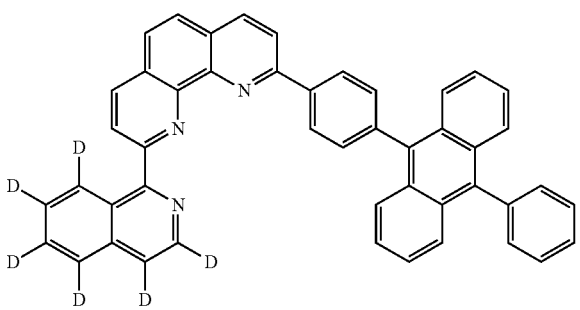

D9

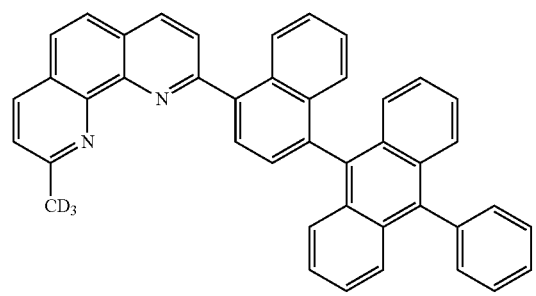
D12
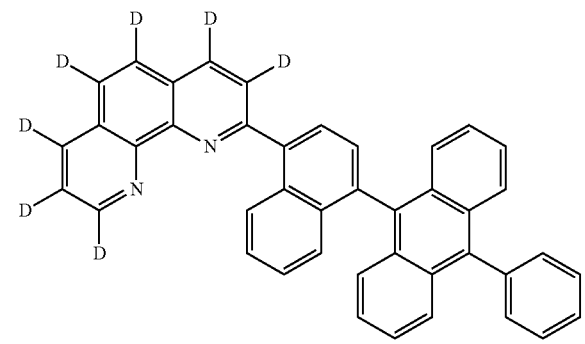
D16
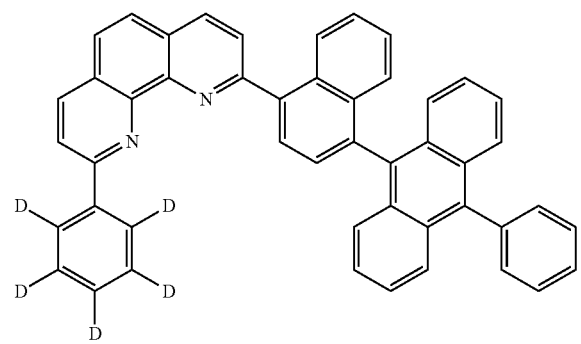
D13
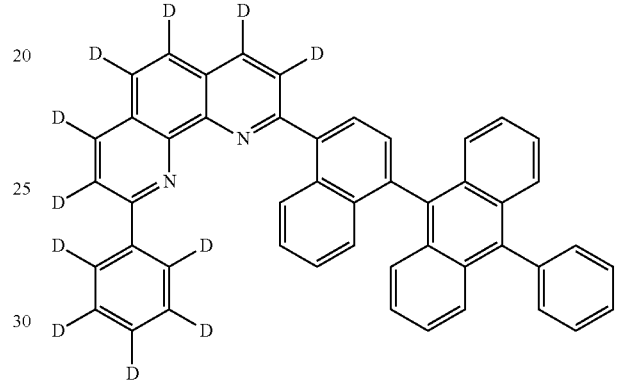
D20
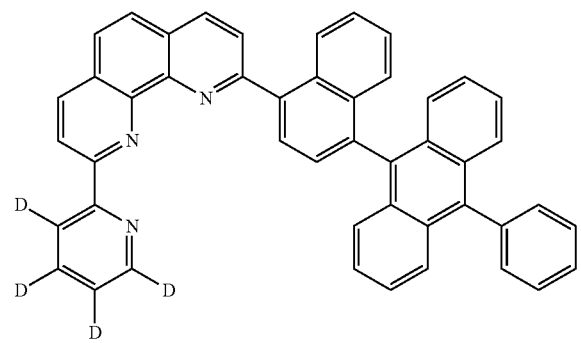
D14
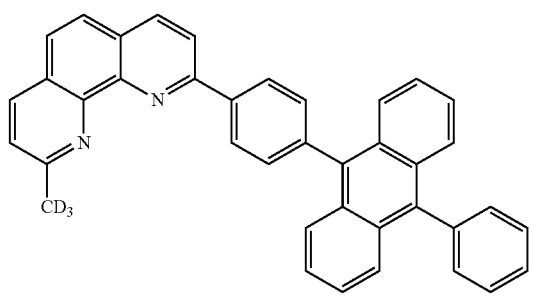
D23
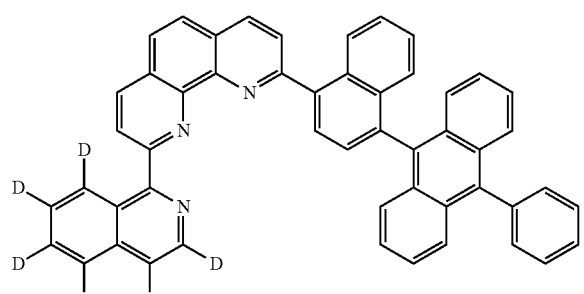
D15
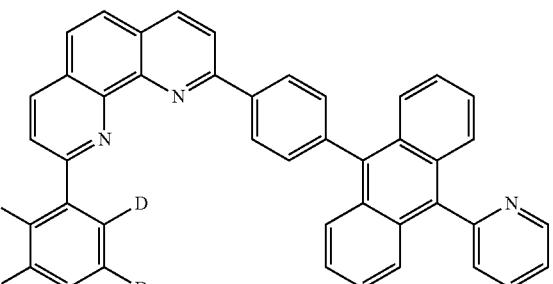
D25

-continued
D26
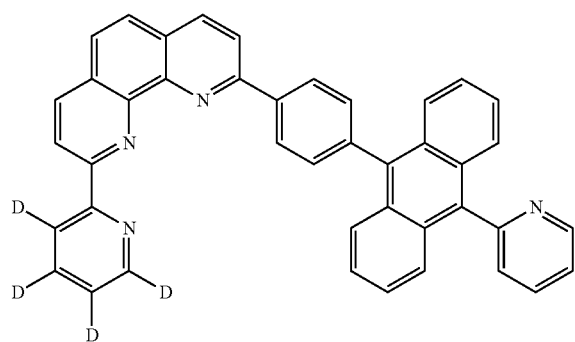
D28
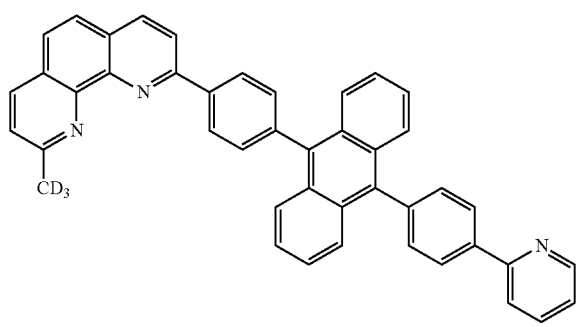
D29
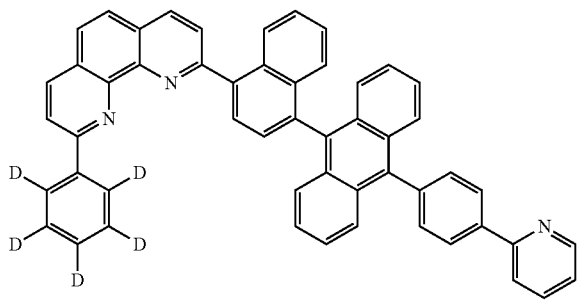
D30
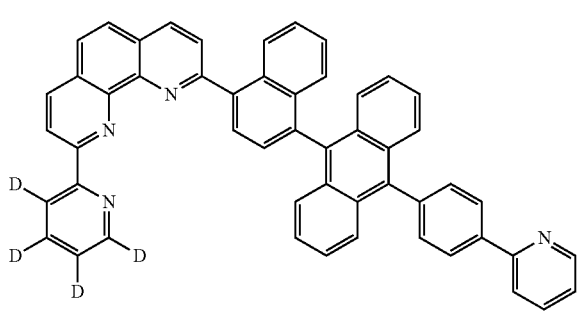
-continued
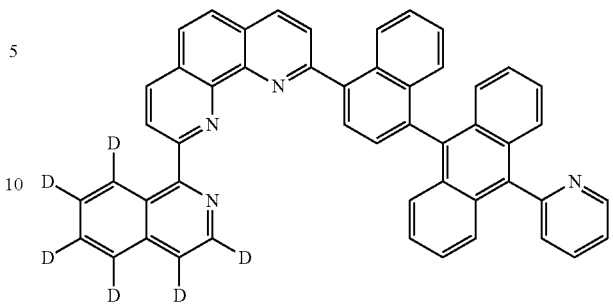
4. The organic compound according to claim 1, wherein L is naphthylene, and $L_2$ is phenyl, and
   wherein d is 0.
5. The organic light emitting diode according to claim 4, wherein the organic compound of Formula 1 is one of compounds:

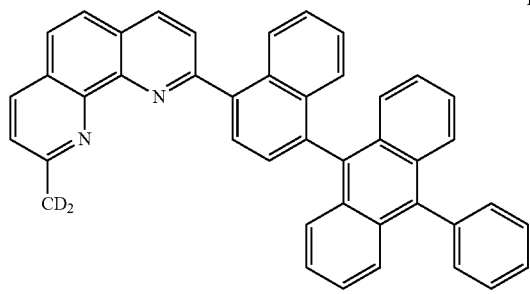

D12

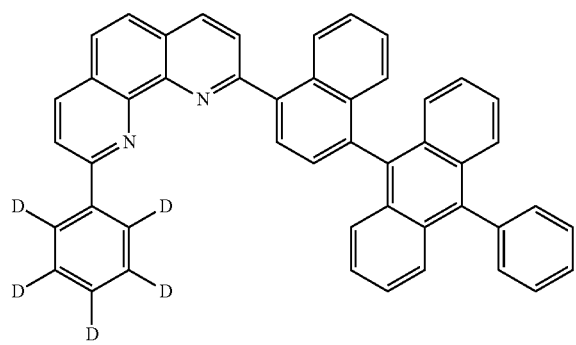

D13

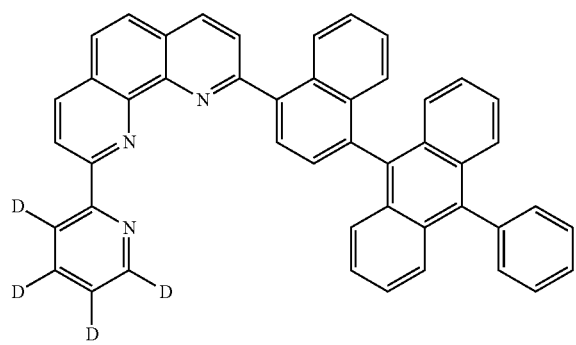

D14

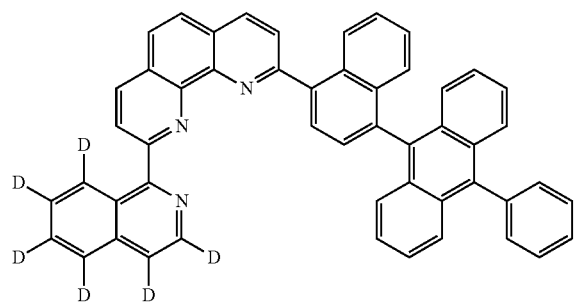

D15

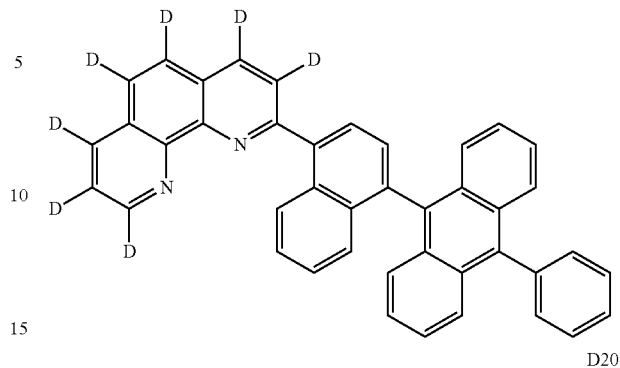

D16

D20

6. An organic light emitting diode, comprising:
a first electrode;
a second electrode facing the first electrode;
an emitting material layer positioned between the first and second electrodes;
a hole auxiliary layer positioned between the first electrode and the emitting material layer; and
an electron auxiliary layer positioned between the emitting material layer and the second electrode,
wherein the electron auxiliary layer includes an organic compound of claim 1.

7. An organic light emitting display device, comprising:
a substrate;
an organic light emitting diode of claim 6 over the substrate; and
a thin film transistor positioned between the substrate and the organic light emitting diode and connected to the organic light emitting diode.

8. An organic light emitting diode, comprising:
a first electrode;
a second electrode facing the first electrode;
a first emitting part positioned between the first and second electrodes and including a first emitting material layer;
a second emitting part positioned between the first emitting material layer and the second electrode and including a second emitting material layer; and
a first charge generation layer between the first and second emitting parts,
wherein the first charge generation layer includes an organic compound of Chemical Formula 1:

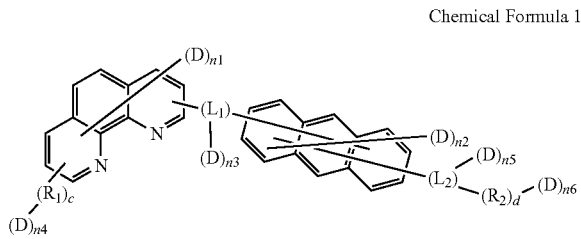

Chemical Formula 1

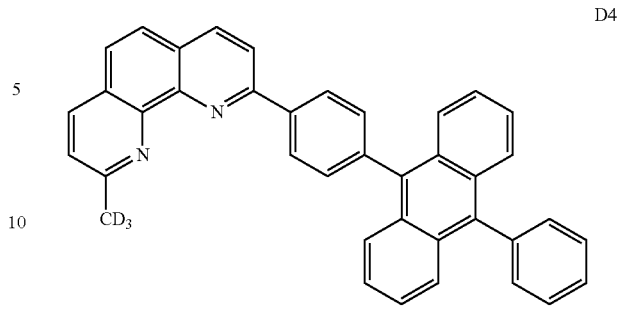

D4

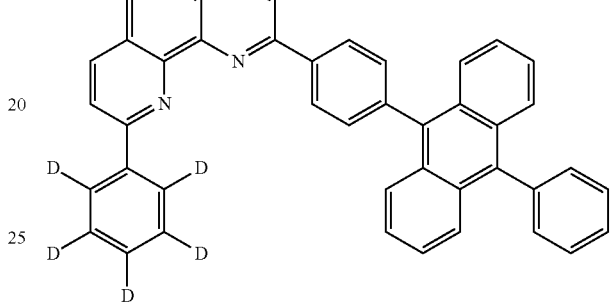

D7 wherein $L_1$ is selected from a C6 to C30 arylene group, and $L_2$ is selected from a C6 to C30 aryl group, a C6 to C30 arylene group, a C5 to C30 heteroaryl group and a C5 to C30 heteroarylene group, and each of $R_1$ and $R_2$ is independently selected from a C1 to C10 alkyl group, a C6 to C30 aryl group and a C5 to C30 heteroaryl group, wherein each of c and d is independently 0 (zero) or a positive integer, and wherein at least one of n1 and n4 is the positive integer, and n2, n5 and n6 are 0.

9. The organic light emitting diode according to claim 8, wherein the first emitting part further includes a first electron auxiliary layer between the first emitting material layer and the first charge generation layer, and the second emitting part further includes a second electron auxiliary layer between the second emitting material layer and the second electrode, and wherein at least one of the first and second electron auxiliary layers includes the organic compound of Chemical Formula 1.

10. The organic light emitting diode according to claim 8, wherein one of the first and second emitting parts emits a blue light, and the other one of the first and second emitting parts emits a yellow-green light.

11. The organic light emitting diode according to claim 8, further comprising:

a third emitting part positioned between the second emitting part and the second electrode and including a third emitting material layer; and a second charge generation layer between the second and third emitting parts, wherein the second charge generation layer includes the organic compound of Chemical Formula 1.

12. The organic light emitting diode according to claim 8, wherein $L_1$ is selected from phenylene and naphthylene, and $L_2$ is selected from phenyl, phenylene, naphthyl, naphthylene, pyridyl and pyridylene, and wherein $R_1$ is selected from methyl, phenyl, naphthyl, pyridyl and isoquinolinyl, and $R_2$ is selected from pyridyl and pyrimidyl.

13. The organic light emitting diode according to claim 8, wherein the organic compound of Formula 1 is one of compounds:

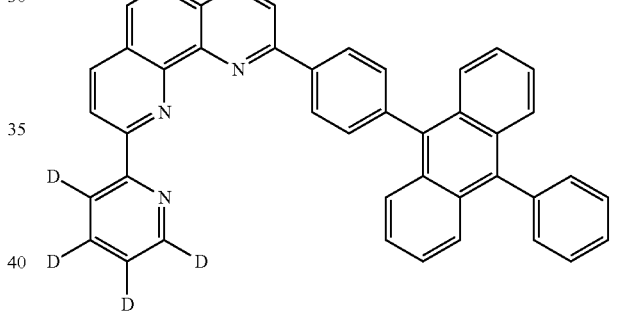

D8

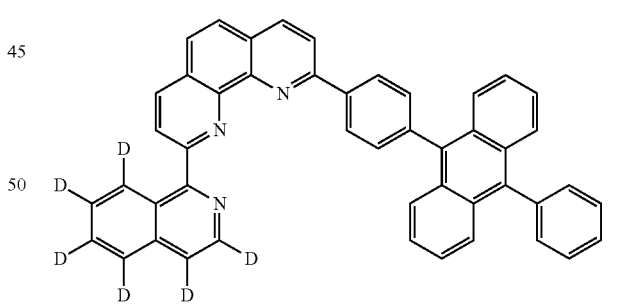

D9

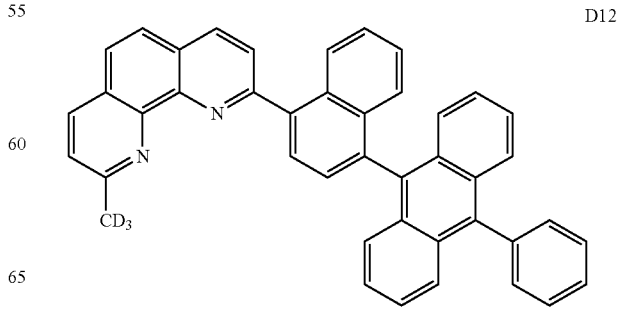

D12

D13
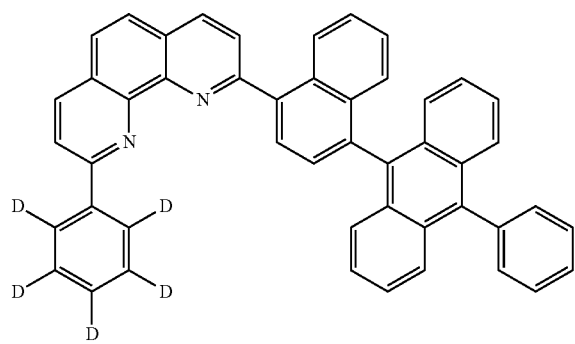
D20
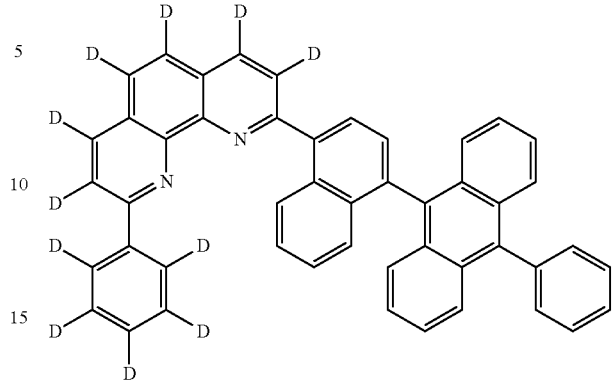
D14
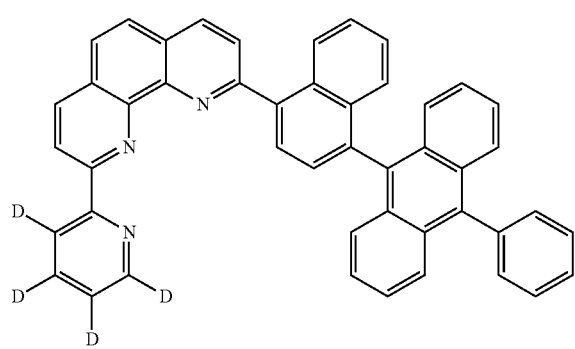
D23
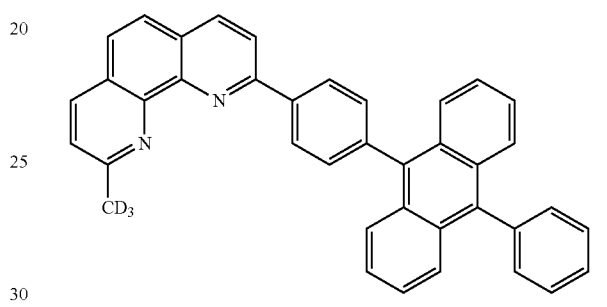
D15
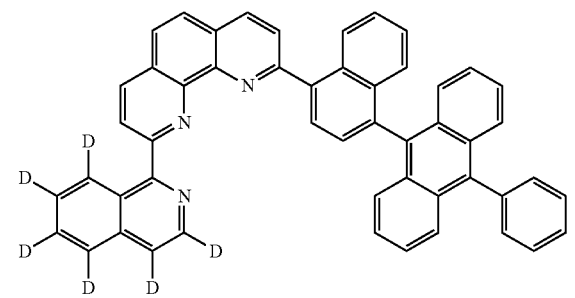
D25
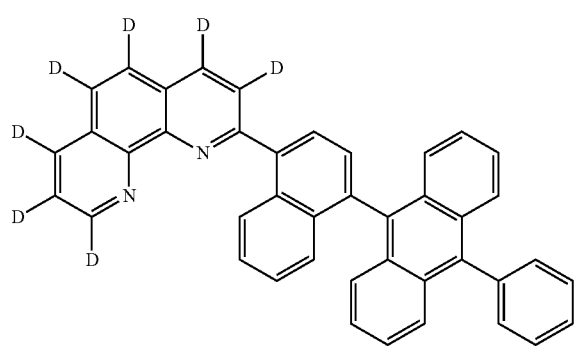
D16
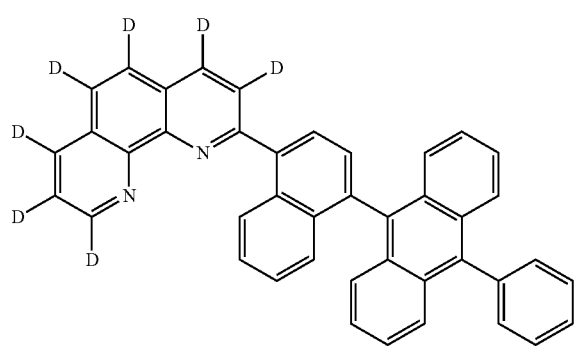
D26
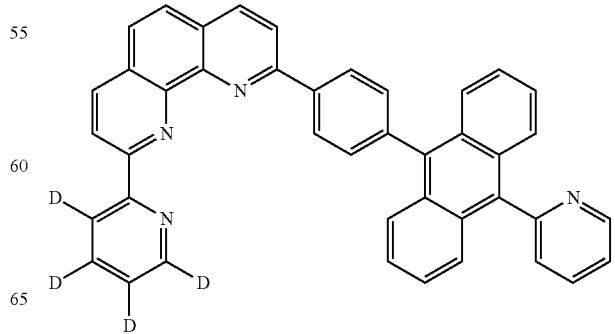

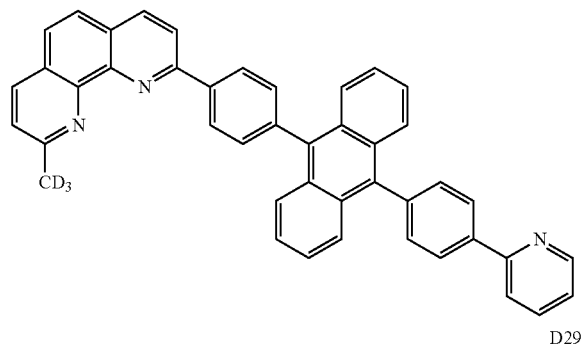
D28
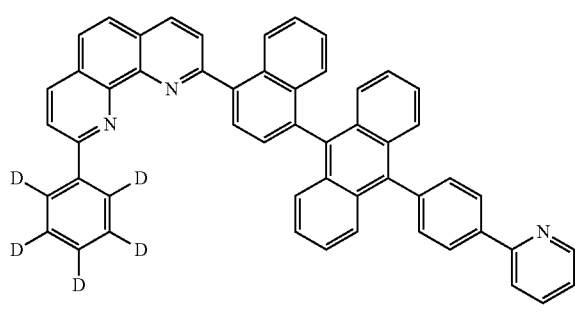
D29
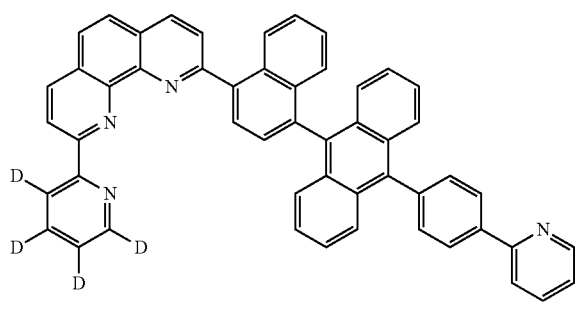
D30
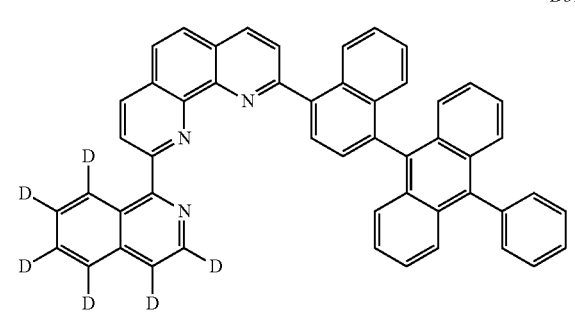
D31
D32
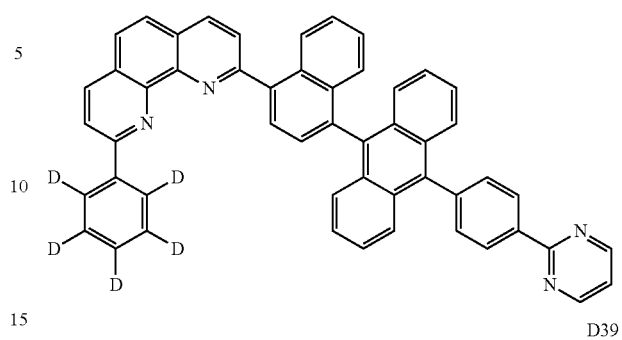
D33
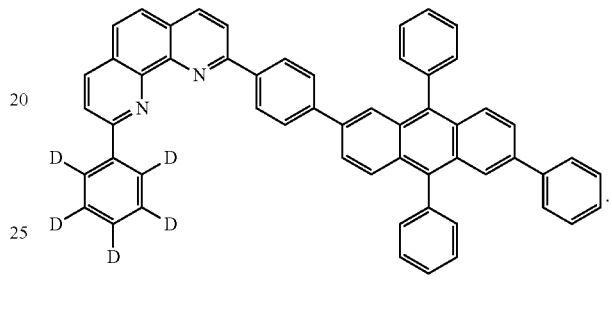
D39
14. The organic light emitting diode according to claim 8, wherein $L_1$ is naphthylene, and $L_2$ is phenyl, and wherein d is 0.
15. The organic light emitting diode according to claim 14, wherein the organic compound of Formula 1 is one of compounds:
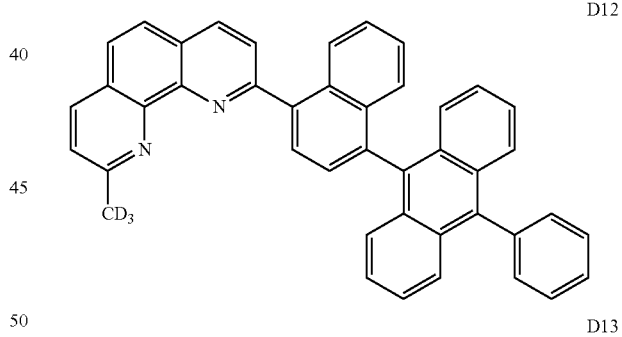
D12
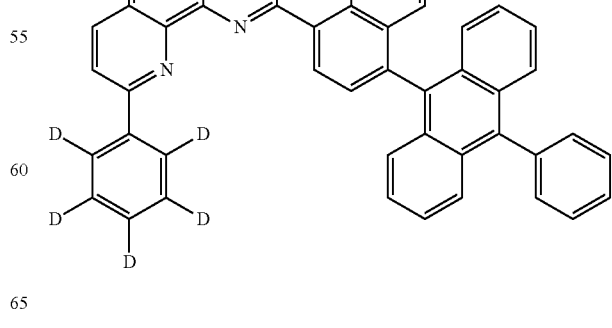
D13

-continued

D14
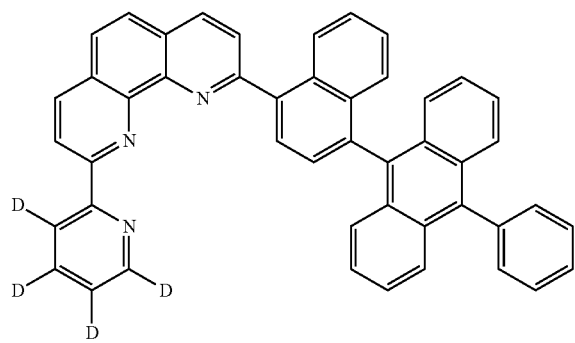

D15
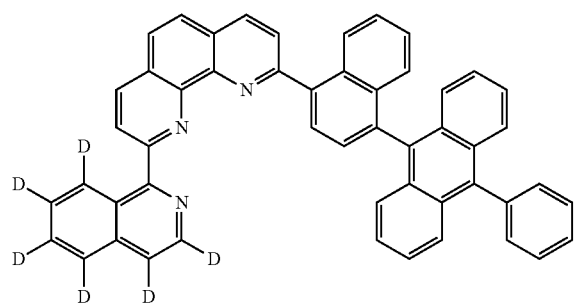

D16
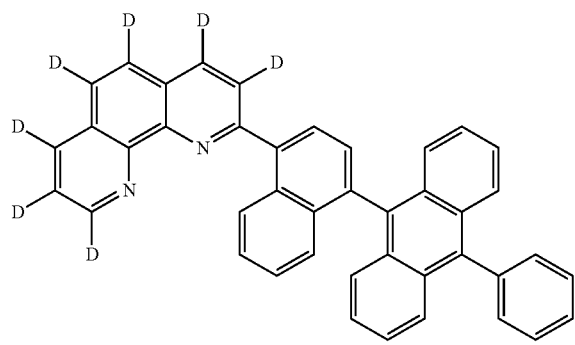

-continued

D20
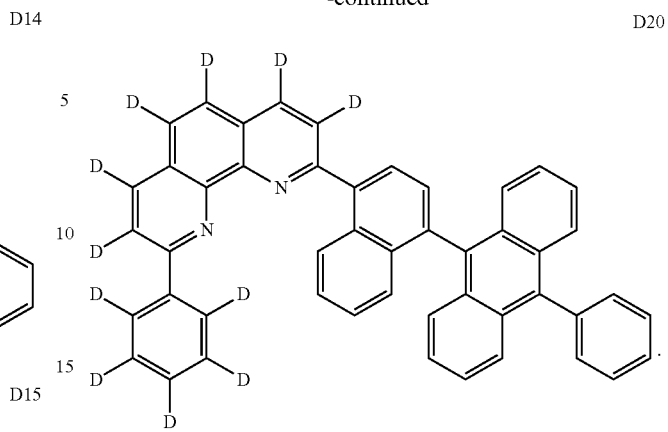

16. An organic light emitting display device, comprising:
a substrate;
an organic light emitting diode of claim 8 over the substrate; and
a thin film transistor positioned between the substrate and the organic light emitting diode and connected to the organic light emitting diode.

17. The organic light emitting display device according to claim 16, wherein a red pixel, a green pixel and a blue pixel are defined on the substrate, and the organic light emitting diode corresponds to each of the red, green and blue pixels, and
wherein the organic light emitting display device further includes:
a color filter layer disposed between the substrate and the organic light emitting diode or over the organic light emitting diode and corresponding to the red, green and blue pixels.

* * * * *